(12) United States Patent
Carney et al.

(10) Patent No.: US 7,732,159 B2
(45) Date of Patent: Jun. 8, 2010

(54) ASSAYS FOR CANCER PATIENT MONITORING BASED ON LEVELS OF ANALYTE COMPONENTS OF THE PLASMINOGEN ACTIVATOR SYSTEM IN BODY FLUID SAMPLES

(75) Inventors: Walter P. Carney, North Andover, MA (US); Peter J. Hamer, Reading, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 11/965,323

(22) Filed: Dec. 27, 2007

(65) Prior Publication Data

US 2008/0113392 A1 May 15, 2008

Related U.S. Application Data

(63) Continuation of application No. 10/375,646, filed on Feb. 27, 2003.

(60) Provisional application No. 60/361,219, filed on Mar. 1, 2002, provisional application No. 60/368,658, filed on Mar. 29, 2002.

(51) Int. Cl.
| | |
|---|---|
| *C12Q 1/00* | (2006.01) |
| *C12Q 33/00* | (2006.01) |
| *C12Q 33/48* | (2006.01) |
| *A01N 37/18* | (2006.01) |
| *A01N 61/00* | (2006.01) |
| *A61K 31/00* | (2006.01) |
| *A61K 38/00* | (2006.01) |
| *A61K 38/28* | (2006.01) |
| *A61K 49/00* | (2006.01) |
| *A61K 51/00* | (2006.01) |
| *A61M 36/14* | (2006.01) |

(52) U.S. Cl. ............... 435/7.92; 435/4; 435/7.1; 435/7.4; 436/63; 436/64; 436/86; 436/174; 514/1; 514/2; 514/4; 424/1.11; 424/9.1; 424/9.21

(58) Field of Classification Search .......... 435/4, 435/7.1, 7.4, 7.92; 436/63, 64, 86, 174; 424/1.11, 424/9.1, 9.21; 514/1, 2, 4
See application file for complete search history.

(56) References Cited

U.S. PATENT DOCUMENTS

| | | | | |
|---|---|---|---|---|
| 4,946,778 | A | 8/1990 | Ladner et al. | 435/69.6 |
| 5,122,464 | A | 6/1992 | Wilson et al. | 435/464 |
| 5,223,409 | A | 6/1993 | Ladner et al. | 435/69.7 |
| 5,403,484 | A | 4/1995 | Ladner et al. | 435/235.1 |
| 5,422,245 | A | 6/1995 | Nielsen et al. | 435/7.4 |
| 5,427,908 | A | 6/1995 | Dower et al. | 435/5 |
| 5,516,637 | A | 5/1996 | Huang et al. | 435/6 |
| 5,571,698 | A | 11/1996 | Ladner et al. | 435/69.7 |
| 5,580,717 | A | 12/1996 | Dower et al. | 435/5 |
| 5,658,727 | A | 8/1997 | Barbas et al. | 435/6 |
| 5,698,426 | A | 12/1997 | Huse | 435/172.3 |
| 5,733,743 | A | 3/1998 | Johnson et al. | 435/69.1 |
| 5,750,753 | A | 5/1998 | Kimae et al. | 556/440 |
| 5,780,225 | A | 7/1998 | Wigler et al. | 435/6 |
| 5,821,047 | A | 10/1998 | Garrard et al. | 435/5 |
| 5,969,108 | A | 10/1999 | McCafferty et al. | 530/387.3 |
| 2002/0012950 | A1 | 1/2002 | Nielsen et al. | 435/7.4 |

FOREIGN PATENT DOCUMENTS

| | | |
|---|---|---|
| WO | WO 86/05807 | 10/1986 |
| WO | WO 89/01036 | 2/1989 |
| WO | WO 02/099114 | 12/2002 |

OTHER PUBLICATIONS

Perkins and Schisterman, "The inconsistency of 'optimal' cutpoints obtained using two criteria based on the receiver operating characteristic curve," *Am J Epidemiol.*, 163(7): 670-675 (Apr. 1, 2006; epub Jan. 12, 2006) Abstract.

Tockman et al., "Considerations in Bringing a Cancer Biomarker to Clinical Application," *Cancer Research(Suppl.)*. 52: 2711s-2718s (May 1, 1992).

(Continued)

*Primary Examiner*—Alana M Harris
(74) *Attorney, Agent, or Firm*—Kevin Stein

(57) ABSTRACT

The present invention describes clinically and medically important methods of examining, screening over time, and monitoring the outcome of a cancer patient who is undergoing treatment or therapy for his or her disease. More specifically, the invention provides a method of monitoring the progression of disease, or the effectiveness of cancer treatment, in a cancer patient by measuring the levels of one or more analytes of the plasminogen activator (uPA) system, namely, uPA, PAI-1 and the complex of uPA:PAI-1, in a sample taken from the cancer patient, preferably, before treatment, at the start of treatment, and at various time intervals during treatment. As a result of performing the method, an increase or elevation in the levels of one or more of the PA system analytes in the cancer patient compared with the levels one or more of the respective PA system analytes in normal control individuals serves as an indicator of cancer advancement or progression and/or a lack of treatment effectiveness for the patient.

34 Claims, 6 Drawing Sheets

OTHER PUBLICATIONS

Konecny et al., "Association of urokinase-type plasminogen activator and its inhibitor with disease progression and prognosis in ovarian cancer," *Clinical Cancer Research: An Official Journal of the American Association for Cancer Research*, Jun. 2001, 7(6), pp. 1743-1749.

Miyake et al., "Elevation of urokinase-type plasminogen activator its receptor densities as new predictors of disease progression and prognosis in men with prostate cancer," *International Journal of Oncology*, Mar. 1999, 14(3), pp. 535-541.

Yang et al., "Urokinase-type plasminogen activator and its receptor in colorectal cancer: independent prognostic factors of metastasis and cancer-specific survival and potential therapeutic targets," *International Journal of Cancer*, Sep. 20, 2000, 89(5), pp. 431-439; Abstract.

Foekens et al., "The urokinase system of plasminogen activation and prognosis in 2780 breast cancer patients," *Cancer Research*, Feb. 1, 2000, 60(3), pp. 636-643; Abstract.

Look et al., "Pooled analysis of prognostic impact of urokinase-type plasminogen activator and its inhibitor PAI-1 in 8377 breast cancer patients," *Journal of the National Cancer Institute*, Jan. 16, 2002, 94(2), pp. 116-128; Abstract.

Broet et al., "Prognostic value of uPA and p53 accumulation measured by quantitative biochemical assays in 1245 primary breast cancer patients: a multicentre study," *British Journal of Cancer*, May 1999, 80(3-4), pp. 536-545; Abstract.

Lox et al., "Tamoxifen-induced changes in the plasma fibrinolytic factors in menopausal women with breast cancer," *Clinical and Applied Thrombosis/Hemostasis*, 1997, 3(4), pp. 234-238; Abstract.

Morii et al., "Prognostic relevance of urokinase type plasminogen activator, its receptor and inhibitors in chondrosarcoma," *Anticancer Research*, Sep. 2000, 20(5A), pp. 3031-3036; Abstract.

Pedersen et al., "Determination of the complex between urokinase and its type-1 inhibitor in plasma from healthy donors and breast cancer patients," *Clinical Chemistry*, Aug. 1999, 45(8), pp. 1206-1213; Abstract.

Nielsen et al., "Preoperative plasma plasminogen activator inhibitor type-1 and serum C-reactive protein levels in patients with colorectal cancer," *Annals of Surgical Oncology*, Sep. 2000, 7(8), Lippincott Williams & Wilkins, pp. 617-623; Abstract.

Supplemental European Search Report Dated Jul. 4, 2006 Corresponding to European Patent Application No. 03 71 1275.

Köhler et al., "Continuous cultures of fused cells secreting antibody of predefined specificity." *Nature*, Aug. 7, 1975, 256(5517), pp. 495-497.

Kozbor et al., "The production of monoclonal antibodies from human lymphocytes," *Immunology Today*, 1983, 4(3), pp. 72-79.

Cole et al., "The EBV-Gybridoma technique and its application to human lung cancer," *Monoclonal Antibodies and Cancer Therapy*, 1985, Alan R. Liss, Inc., New York, pp. 77-96.

Andreasen et al., "The Urokinase-type plasminogen activator system in cancer metastasis: a review," *International Journal of Cancer*, Jul. 3, 1997, 72(1), pp. 1-22.

Dewitte et al., "Prognostic impact of urokinase-type plasminogen activator (uPA) and its inhibitor (PAI-1) in cytosols and pellet extracts derived from 892 breast cancer patients," *British Journal of Cancer*, Mar. 1999, 79(7/8), pp. 1190-1198.

Liotta et al., "Role of collagenases in tumor cell invasión," *Cancer Metastasis Review*, 1982, 1(1), Martinus Nijhoff Publishers, the Hague, the Netherlands, pp. 277-288.

Danø et al., "Plasminogen activators, tissue degradation, and cancer," *Advances in Cancer Research*, Klein et al. (eds.), 1985, 44, Academic Press, Inc., pp. 139-266.

Mignatti et al., "Biology and biochemistry of proteinases in tumor invasion," *Physiological Reviews.*, Jan. 1993, 73(1), The American Physiological Society, pp. 161-195.

Grondahl-Hansen et al., "Localization of urokinase-type plasminogen activator in stromal cells in adenocarcinomas of the colon in humans," *American Journal of Pathology*, Jan. 1991, 138(1), pp. 111-117.

Pyke et al., "The plasminogen activation system in human colon cancer: Messenger RNA for the inhibitor PAI-1 is located in endothelial cells in the tumor stroma," *Cancer Research*, Aug. 1, 1991, 51(15), pp. 4067-4071.

Bacharach et al., "In vivo patterns of expression of urokinase and its inhibitor PAI-1 suggest a concerted role in regulating physiological angiogenesis," *Proceedings of the National Academy of Sciences of the USA*, Nov. 5, 1992, 89(22), pp. 10686-10690.

Duffy, "The role of proteolytic enzymes in cancer invasion and metastasis," *Clinical Experimental Metastasis*, May 1992, 10(3), Rapid Communications of Oxford, pp. 145-155.

Pöllänen et al., "Directed plasminogen activation at the surface of normal and malignant cells," *Advances in Cancer Research*, 1991, 57, Academic Press, Inc., pp. 273-328.

Ossowski, "Invasion of connective tissue by human carcinoma cell lines: requirement for urokinase, urokinase receptor, and interstitial collagenase," *Cancer Research*, Dec. 15, 1992, 52(24), pp. 6754-6760.

Blasi et al., "Urokinase-dependent cell surface proteolysis and cancer," *Seminars in Cancer Biology: The Role of Proteases in Cancer*, Apr. 1990, 1 (2), pp. 117-126.

Chapman et al., "Plasminogen activators, integrins, and the coordinated regulation of cell adhesion and migration," *Current Opinion in Cell Biology*, Oct. 1997, 9(5), Current Biology, Ltd., pp. 714-724.

Deng et al., "The PAI-1/vitronectin interaction: two cats in a bag?" *Thrombosis and Haemostasis*, Jul. 1995, 74(1), pp. 66-70.

Lawrence et al., "Localization of vitronectin binding domain in plasminogen activator inhibitor-1," *Journal of Biological Chemistry*, May 27, 1994, 269(21), pp. 15223-15228.

Bajou et al., "Absence of host plasminogen activator inhibitor 1 prevents cancer invasion and vascularization," *Nature Medicine*, Aug. 1998, 4(8), pp. 923-928.

Kristensen et al., "Plasminogen activator inhibitor-type 1 in Lewis lung carcinoma," *Histochemistry*, Apr. 1990, 93(6), Springer International, pp. 559-566.

Cubellis et al., "Receptor-mediated internalization and degradation of urokinase is caused by its specific inhibitor PAI-1," *The EMBO Journal*, Apr. 1990, 9(4), IRL Press at Oxford University Press, pp. 1079-1085.

Markus et al., "Plasminogen activator secretion of human tumors in short-term organ culture, including a comparison of primary and metastatic colon tumors," *Cancer Research*, Nov. 1983, 43(11), American Association for Cancer Research, pp. 5517-5525.

Pyke et al., "Rapid communication: urokinase-type plasminogen activator is expressed in stromal cells and its receptor in cancer cells at invasive foci in human colon adenocarcinomas," *American Journal of Pathology*, May 1991, 138(5), pp. 1059-1067.

Setyono-Han et al., "Anti-tumor and anti-metastatic activity of the urokinase/plasmin inhibitor, WX-UK1, as single agent or in combination with epirubicin in the rat BN-472 mammary carcinoma model," *Proceedings of American Association for Cancer Research: 92$^{nd}$ Annual Meeting*, Mar. 24-28, 2001, 42, New Orleans, LA, p. 69 (Abstract #371).

Probst et al., "Small molecule approach to inhibit the urokinase-type plasminogen activator system," *Proceedings of American Association for Cancer Research: 92$^{nd}$ Annual Meeting*, Mar. 24-28, 2001, 42, New Orleans, LA, p. 69 (Abstract #370).

Brinkman et al., "Phage display of disulfide-stabilized Fv fragments," *Journal of Immunological Methods*, 1995, 182(1), Elsevier Science B.V., pp. 41-50.

Ames et al., "Conversion of murine Fabs isolated from a combinatorial phage display library to full length immunoglobulins," *Journal of Immunological Methods*, 1995, 184(2), Elsevier Science B.V., pp. 177-186.

Kettleborough et al., "Isolation of tumor cell-specific single-chain Fv from immunized mice using phage-antibody libraries and the reconstruction of whole antibodies from these antibody fragments," *European Journal of Immunology*, Apr. 1994, 24(4), pp. 952-958.

Persic et al., "An integrated vector system for the eukaryotic expression of antibodies or their fragments after selection from phage display libraries," *Gene: an International Journal on Genes and Genomes*, 1997, 187(1), Elsevier Science B.V., pp. 9-18.

Burton et al., "Human antibodies from combinatorial libraries," *Advances in Immunology*, 1994, 57, Academic Press, Inc. pp. 191-280.

Sutcliffe et al., "Antibodies that react with predetermined sites on proteins," *Science*, Feb. 11, 1983, 219(4585), pp. 660-666.

Wilson et al., "The structure of an antigenic determinant in a protein," *Cell*, Jul. 1984, 37(3), pp. 767-778.

Francis et al., "Immunological priming with synthetic peptides of foot-and-mouth disease virus," *Journal of General Virology*, Nov. 1985, 66(11), the Society for General Microbiology, Great Britain, pp. 2347-2354.

Foecking et al., "Powerful and versatile enhancer-promoter unit for mammalian expression vectors," *Gene: an international journal focusing on gene cloning and gene structure and function*, 1986, 45(1), Elsevier Science Publishers B.V. (Biomedical Division), pp. 101-105.

Cockett et al., "High level expression of tissue inhibitor of metalloproteinases in Chinese hamster ovary cells using glutamine synthetase gene amplification," *Bio/Technology: The International Monthly for Industrial Biology*, Jul. 1990, 8(1), pp. 662-667.

Andreasen et al., "Plasminogen activator inhibitor from human fibrosarcoma cells binds urokinase-type plasminogen activator, but not its proenzyme," *The Journal of Biological Chemistry*, Jun. 15, 1986, 261(17), The American Society of Biological Chemists, Inc., pp. 7644-7651.

Del Villano et al., "Radioimmunometric assay for a monoclonal antibody-defined tumor marker, CA 19-9," *Clinical Chemistry*, Mar. 1983, 29(3), pp. 549-552.

Ritts Jr. et al., "Initial clinical evaluation of an immunoradiometric assay for CA 19-9 using the NCI serum bank," *International Journal of Cancer*, Mar. 15, 1984, 33(3), pp. 339-345.

Rule, "Carcinoembryonic antigens (CEA)," *Methods in Clinical Chemistry*, Chapter 90, 1987, The C.V. Mosby Company, pp. 702-713.

Plasma PAI-1 Increases by Cancer Type

Mean Plasma uPA:PAI-1 Complexes

ASSAYS FOR CANCER PATIENT MONITORING BASED ON LEVELS OF ANALYTE COMPONENTS OF THE PLASMINOGEN ACTIVATOR SYSTEM IN BODY FLUID SAMPLES

REFERENCE TO PRIOR APPLICATIONS

This application is a continuation of co-pending U.S. patent application Ser. No. 10/375,646, filed Feb. 27, 2003, to which priority under 35 U.S.C. §120 is claimed, and which claims the benefit under 35 U.S.C. §119(e) of U.S. provisional Application Ser. Nos. 60/361,219, filed Mar. 1, 2002, and 60/368,658, filed Mar. 29, 2002, all of which are incorporated herein by reference.

FIELD OF THE INVENTION

The present invention relates to assays for monitoring or assessing the progress of cancer patients during a course of disease or disease treatment or therapy by determining levels of one or more cancer analytes, i.e., components of the plasminogen activator (PA) system, compared to the levels of one or more of these PA system components in normal control individuals. According to the methods described herein, the determination of increases in the levels of one or more of urokinase plasminogen activator (uPA), PA inhibitor-1 (PAI-1), or a complex of uPA and PAI-1 (the uPA:PAI-1 complex), compared with the levels of these respective analytes in normal controls is indicative of poor patient and/or treatment outcome relative to disease status.

BACKGROUND OF THE INVENTION

The plasminogen activator (PA) system involves the serine proteases plasmin and urokinase plasminogen activator (uPA); the serpins $\alpha_2$-antiplasmin, plasminogen activator inhibitor type-1 (PAI-1) and plasminogen activator inhibitor type-2 (PAI-2); and the uPA receptor (uPAR). During the past decade, evidence for the involvement of components of the PA system in cancer metastasis has increased and it is believed that the uPA-mediated pathway of plasminogen activation is active in the cancer process. (P. A. Andreasen et al., 1997, *Int. J. Cancer*, 72:1-22).

Proteolytic enzymes, such as those of the PA system, are involved in cancer invasion and metastasis by virtue of their ability to invade and degrade basement membranes and extracellular matrix proteins that surround normal tissue (J. H. DeWitte et al., 1999, *Br. J. Cancer*, 79:1190-1198; L. A. Liotta et al., 1982 *Cancer Metastasis Rev.*, 1:277-297; K. Dano et al., 1985, *Adv. Cancer Res.*, 44:139-266; P. Mignatti and D. B. Rifkin, 1993, *Physiol. Rev.*, 73:161-195; and P. A. Andreasen et al., 1997, Ibid.). Immunohistochemical and in situ observations of uPA, plasminogen and PAI-1 distribution in adenocarcinomas show that proteinase degradation of the extracellular matrix occurs as localized invasive foci (J. Grøndahl-Hansen et al., 1991, *Am. J. Pathol.*, 138:111-117; C. Pyke et al., 1991, *Proc. Third Intl. Workshop on the Molecular and Cellular Biology of Plasminogen Activation:Elsinore*, 45; C. Pyke et al., 1991, *Cancer Res.*, 51:4067-4071). In the case of angiogenesis, there is also a functional interaction between uPA and PAI-1 (E. Bacharach et al., 1992, *Proc. Natl. Acad. Sci. USA*, 89:10686-10690).

Urokinase plasminogen activator (uPA) is a 52 kilodalton (kDa) serine protease that is secreted by cells as an inactive, single-chain precursor called pro-uPA. Enzymatic cleavage of pro-uPA at lysine 158 produces an active heterodimer, called high molecular weight uPA (HMW-uPA), which contains two subunits A and B. When pro-uPA is secreted from cells, it binds to uPAR on the cell surface through an EGF-like domain on the A chain. Subsequent binding of plasmin to uPA can convert pro-uPA into the proteolytically active heterodimer. In turn, active uPA rapidly converts the inactive plasmin precursor, plasminogen, into enzymatically active plasmin, which is directly involved in extracellular matrix degradation, as well as in the activation of other pro-collagenases, some prometalloproteases and latent growth factors (K. Dano et al., 1985, Ibid.; M. J. Duffy, 1992, *Clin. Exp. Metastasis*, 10:145-155; J. R. Pollanen et al., 1991, *Adv. Cancer Res.*, 57:273-282; L. Ossowski, 1992, *Cancer Res.*, 52:D: 6754-6760; P. Mignatti and D. B. Rifkin, 1993, Ibid.; and P. A. Andreasen et al., 1997, Ibid.). The additional cleavage of uPA after lysine 135 releases the 17 kDa amino terminal fragment (ATF), leaving the carboxy-terminal low molecular weight uPA (LMW-uPA, 33 kDa), which retains full catalytic activity. (F. Blasi et al., 1990, *Seminars in Cancer Biology*, 1:117-126).

Both PAI-1 and PAI-2 bind to the catalytically active B chain of uPA to regulate its enzymatic activity. By forming complexes with uPA bound to uPAR on the cell surface, PAI-1 promotes the clearance of proteolytic activities from the cell surfaces, as well as the recycling of unbound uPAR back to the cell surface, thereby regulating the overall invasive and metastatic behavior of cancer cells. (P. A. Andreasen et al., 1997, Ibid. and H. A. Chapman et al., 1997, *Curr. Op. Cell Biol.*, 9:714-724). PAI-1 is a 50 kDa glycoprotein serine protease inhibitor that is the principal physiological inhibitor of both forms of the plasminogen activators PA and tissue plasminogen activator (TPA). PAI-1 is secreted in an active form which spontaneously converts to a latent form (G. Deng et al., 1995, *Thrombosis and Haemostasis*, 74:66-70), but it can be stabilized in the active form by binding to the plasma protein vitronectin (D. A. Lawrence et al., 1994, *J. Biol. Chem.*, 269:15223-15228). Both tumor cells and capillary endothelial cells express higher levels of PAI-1 than do other cell types (K. Bajou et al., 1998, *Nature Medicine*, 4:923-928). High levels of PAI-1 are thought to protect the tumor stroma from degradation by the high amounts of uPA secreted by cells. (E. Bacharach et al., 1992, *Proc. Natl. Acad. Sci. USA*, 89:10686-10690; P. Kristensen et al., 1990, *Histochemistry*, 93:559-566). Elevated levels of PAI-1 may also contribute to tumor-induced angiogenesis by protecting the extracellular matrix surrounding the tumor from proteolytic degradation (C. Pyke et al., 1991, *Cancer Res.*, 51:4067-4071). When active uPA is bound to its receptor, the subsequent binding of PAI-1 results in internalization and degradation of the uPA:uPAR:PAI-1 complex. (M. V. Cubellis et al., 1990, *The EMBO J.*, 9:1079-1085). This down-regulation of uPA decreases the amount of active uPA on the cell surface.

Secreted uPA can originate from several cell types, including tumor cells (G. Markus et al., 1983, *Cancer Res.*, 43:5517-5525), adjacent stromal cells and fibroblasts (C. Pyke et al., 1991, *Am. J. Pathol.*, 138:1059-1067). Early studies of PAI-1 and uPA:PAI-1 complexes in oncogenesis involved the use of tumor lysates and cytosols; it was found that PAI-1 levels in tumor lysates had a prognostic correlation in breast cancer. Tumor levels of PAI-1 were also analyzed in lung cancer, colon cancer and renal cell carcinoma; this inhibitor has become an unlikely prognostic marker in tumor tissue for cancer metastasis. (P. A. Andreasen et al., 1997, Ibid.).

Because the PA system components are intricately involved in the process of cancer and cancer spread in a variety of cancer types, which afflict both genders, it is a problem in the art to be able to accurately and sensitively screen over time to determine and monitor those individuals who are likely to respond, and/or who are responding to, (or not responding to), or benefiting from (or not benefiting from), anti-cancer therapy(ies), or combination therapies, particularly, molecularly targeted therapies to the plasminogen activation system. The present invention solves such a problem by providing a sensitive and reliable assay method, preferably an immunoassay, to determine levels of PA system analyte components in body fluid samples of cancer patients compared to the levels of these respective PA system components in normal individuals. In addition, the present invention is advantageous in that it is employed to monitor cancer patients undergoing cancer or anti-neoplastic therapies to treat cancers associated with the activity of PA system components to assist in the determination and examination of cancer treatment regimens and patient progress and/or outcome during the course of disease and/or anti-cancer therapy (ies).

BRIEF SUMMARY OF THE INVENTION

The present invention provides assays (methods) for the analysis of body fluid samples from cancer patients to detect and measure levels of PA system analytes, namely, uPA, PAI-1 and the complex of uPA:PAI-1, to determine whether the levels of one or more of these analytes is increased in cancer patients compared to their respective levels in normal individuals. The determination of a measurable increase in the levels of one or more of the PA system analytes in a cancer patient's body fluid sample, e.g., a plasma or serum sample, compared to the levels of these PA system analytes in normal controls, affords a means of monitoring the patient's disease status, and/or patient response or benefit to cancer therapy, both conventional anti-cancer and anti-neoplastic disease treatments and therapies, e.g., drugs, hormones, and the like, and treatments and therapies that more particularly target one or more of the PA system components.

A particular aspect of the present invention provides a monitoring method in which plasma or serum levels of uPA, PAI-1, and the uPA:PAI-1 complex in patients having a cancer or neoplastic disease, for example, of the colon, prostate, breast (mammary), or lung, are monitored during the course of cancer or anti-neoplastic treatment, and preferably prior to, or just at, the start of treatment. The determination of an increase in the plasma or serum levels of one or more of these PA system analytes in the cancer patient compared to the normal levels of one or more of the PA system analytes allows the practitioner to be able to evaluate the patient's disease progression and/or outcome of disease. For example, based on the monitoring of a patient's PA system analyte levels over time compared to normal levels of the analytes, as well as to the patient's own prior-determined levels, a determination can be made as to whether a treatment regimen should be changed, i.e., to be more aggressive or less aggressive; to determine if the patient is responding favorably to his or her treatment; and/or to determine disease status, such as advanced stage or phase of the cancer, or a remission, reduction or regression of the cancer or neoplastic disease.

Another aspect of the present invention provides normal plasma or serum values for uPA, PAI-1 and the uPA:PAI-1 complex in healthy individuals. In accordance with the invention, normal ranges of plasma or serum levels for uPA, PAI-1 and a complex of uPA:PAI-1 have been established for normal males, normal females and both normal males and normal females. (Tables 1-3). Normal levels of uPA in serum are provided; normal levels of PAI-1 and the uPA:PAI-1 complex in plasma are provided.

In yet other aspects of the present invention, methods of monitoring cancer or neoplastic disease in patients to select those patients who are most likely to benefit from anti-cancer or anti-neoplastic disease therapies, including those therapies that specifically target components of the PA system, are provided and performed as described herein. According to the invention, the methods involve the monitoring of the individual PA system components, namely, uPA, PAI-1, and the uPA:PAI-1 complex, either alone, or in combination with each other, to provide individualized assessment of patient status before, during and after cancer treatment; and specialized cancer treatment for the cancer patient, based on a determination of the levels of one or more of the PA system components relative to the levels of these components in normal controls.

Further aspects, features and advantages of the present invention will be better understood upon a reading of the detailed description of the invention when considered in connection with the accompanying figures/drawings.

DETAILED DESCRIPTION OF THE INVENTION

Figure 1:
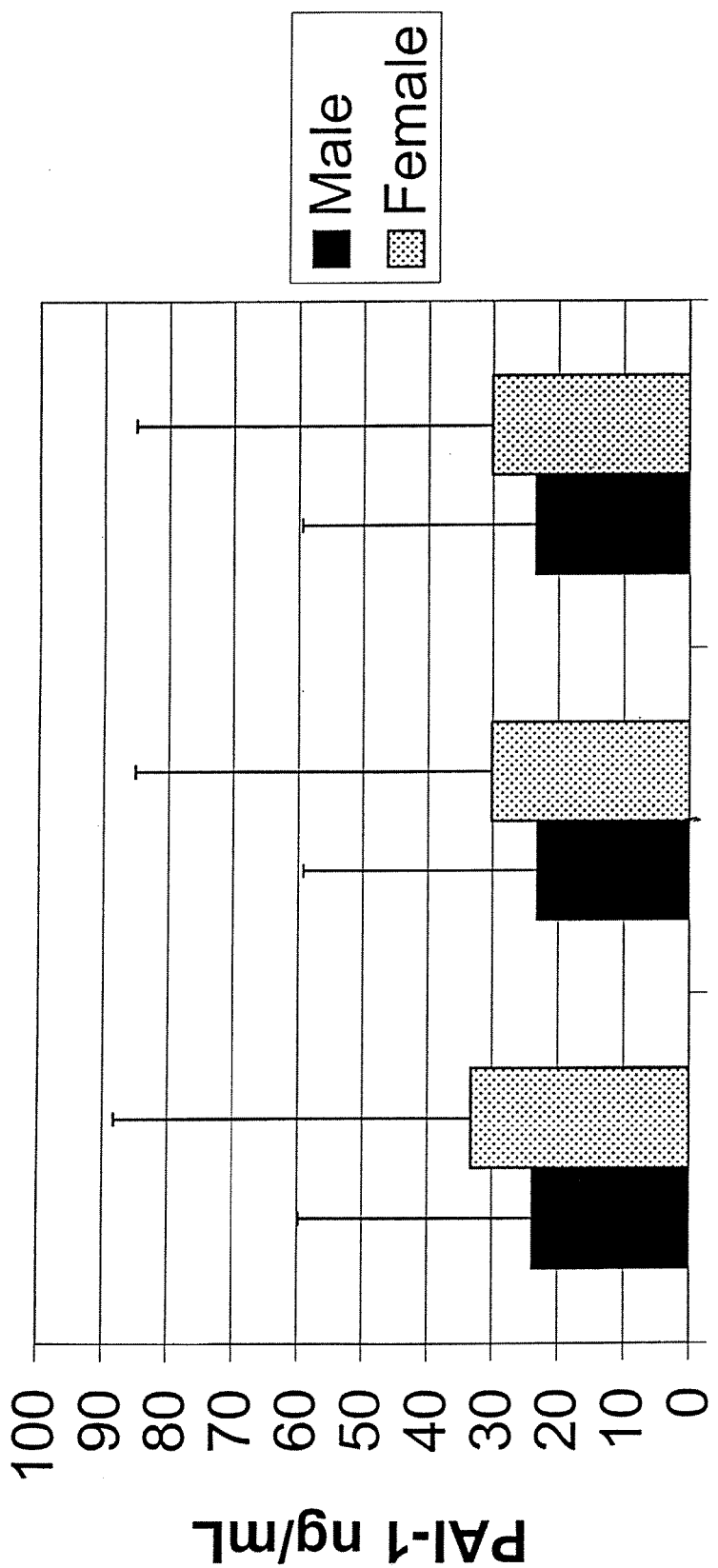
FIG. 1 illustrates the PAI-1 levels in normal human plasma. For operator 1, the PAI-1 level in normal female plasma was determined to be 33.29 ng/ml and the PAI-1 1 level in normal male plasma was determined to be 23.82 ng/ml; for operator 2, the PAI-1 level in normal female plasma was determined to be 30.13 ng/ml and the PAI-1 1 level in normal male plasma was determined to be 23.18 ng/ml; for operator 3, the PAI-1 level in normal female plasma was determined to be 30.12 ng/ml and the PAI-1 1 level in normal male plasma was determined to be 23.46 ng/ml.

The present invention relates to an accurate and sensitive method of examining cancer or neoplastic disease status, as well as screening over time and monitoring, cancer patients by measuring the levels of one or more of the PA system analytes uPA, PAI-1, and the uPA:PAI-1 complex in a patient's body fluid sample to determine if the patient has increased levels of these PA system analytes relative or compared to the levels of these analytes in normal individuals. The determination of higher or increased plasma or serum levels of one or more of the uPA, PAI-1, or uPA:PAI-1 complex analytes in a sample from a cancer patient compared with the levels of one or more of these analytes in normal individuals, (i.e., a comparison with a normal range, a normal value, or a normal cutoff value), informs the patient, physician, and/or clinician as to one or more of the following parameters: the status of the patient's disease state; the response of the patient to cancer or anti-neoplastic treatment or therapy; the benefit or efficacy of a treatment or therapy for the patient; the progress of therapy, or lack thereof, and/or the clinical course and/or outcome of the disease.

Preferably, according to this invention, the uPA analyte is determined in a body fluid sample from a human patient; non-limiting examples of such samples include pleural fluid samples, pulmonary or bronchial lavage fluid samples, synovial fluid samples, peritoneal fluid samples, bone marrow aspirate samples, lymph, cerebrospinal fluid, ascites fluid samples, amniotic fluid samples, sputum samples, bladder washes, semen, urine, saliva, tears, blood, and its components serum and plasma, and the like. Serum is a preferred body fluid sample for uPA determination, as serum allows for real-time assessment of the plasminogen activation status of a cancer patient, allows for repeated testing for patient monitoring and can be performed in a standardized and quantitative manner.

Also in accordance with this invention, the PAI-1 and the uPA:PAI-1 complex analytes are optimally determined using plasma samples. Therefore, it is to be understood that in the methods described herein, a plasma sample is optimally used for the determination/measurement of both PAI-1 and the uPA:PAI-1 complex analytes, while serum, or another body fluid sample, is suitable for the determination/measurement of the uPA analyte. For analyses of uPA according to the present invention, plasma and serum levels of the uPA analyte in the same sample are equivalent. For PAI-1 and uPA:PAI-1 complex analyses according to the present invention, plasma is used as a valid sample type. It is also to be understood that body fluid samples from other mammals, e.g., non-human primates, and other large and small animals, are also able to be assayed and monitored by the methods as described herein.

In accordance with the present invention, a patient whose sample is to be monitored or assessed can be undergoing, or ready to undergo, conventional cancer therapy and/or more unconventional anti-PA system therapies, such as those described herein. The present methods also encompass a method of determining patient outcome or disease severity, based on the finding of increased plasma or serum levels of the PA system analytes in cancer patients compared to the plasma levels of these analytes in normal individuals. The methods are particularly useful in light of the advent of more unconventional cancer therapies, e.g., small molecule inhibitors of PA system components, that are specifically targeted to the plasminogen activation system.

As one nonlimiting example, a urokinase/plasmin inhibitor WX-UK1 (a synthetic amidino phenylalanine-type serine protease inhibitor drug), either used alone or in combination with epirubicin (an anthracycline-type cytostatic commonly used in the treatment of human mammary cancers), has been shown to have anti-tumor and anti-metastatic activity. (Wilex Biotechnology, Munich, Germany; B. Setyono-Han et al., 2001, *Proc. Am. Assoc. Cancer Res.*, 42:69 (Abstract #371), from the 2001 *Meeting of the AACR*). As another example, not meant to be limiting, other small molecule inhibitors were found to inhibit components of the PA system. One such molecule, a peptide-based uPA receptor antagonist (WX-360), was found to intervene with the uPA/uPAR processes required for tumor angiogenesis; a second molecule, WX-UK1, a synthetic serine protease inhibitor based on 3-amidino-phenylalanine, was found to reduce the growth rate of primary tumors and the number of metastatic foci at distant sites in syngeneic rat models of mammary and pancreatic cancers; a third molecule, WX-293 was shown to be a highly selective inhibitor of uPA. (Wilex Biotechnology, Munich, Germany; J. C. Probst et al., 2001, *Proc. Am. Assoc. Cancer Res.*, 42:69 (Abstract #370), from the 2001 *Meeting of the AACCR*).

The present invention encompasses the use of the described in vitro analysis methods to assess uPA, PAI-1 and uPA:PAI-1 complex levels in patients having a variety of cancers or neoplastic diseases, particularly those cancers or neoplastic diseases that are associated with the abnormal expression or activity of one or more components of the PA system. Non-limiting examples of cancers and neoplastic diseases embraced by this invention include solid tumor cancers, and cancers of the skin, lung, trachea, breast (mammary), prostate, gynecological cancers, such as those of the cervix, ovary, vulva, vagina and endometrium, urinary tract cancers, such as those of the bladder; and cancers of the pancreas, gall bladder, thyroid, esophagus, head and neck, brain, kidney, liver, stomach (gastric), gastrointestinal, rectum and colon (colorectal).

According to this invention, the PA system analytes uPA, PAI-1 and the uPA:PAI-1 complex can be measured in a sample, e.g., a plasma or serum sample depending upon the analyte, using assays that specifically detect these components, for example, radioisotopic immunoassays or non-isotopic immunoassays, e.g., fluorescent immunoassays and enzymatic immunoassays, such as an enzyme linked immunoassay (ELISA), as are commercially available, known and practiced in the art. (See, e.g., U.S. Pat. No. 5,422,245 to Lars S. Nielsen et al.; U.S. Patent Application No. 20020012950 A1 of Lars S. Nielsen et al.; uPA Microtiter ELISA (Bayer Diagnostics/Oncogene Science, Cambridge, Mass.); PAI-1 Microtiter Microtiter ELISA (Bayer Diagnostics/Oncogene Science, Cambridge, Mass.); Human uPA:PAI-1 Complex Quantitative ELISA (Bayer Diagnostics/Oncogene Science, Cambridge, Mass.); and uPA, PAI-1, and uPA:PAI-1 ELISA assays (American Diagnostica, Greenwich, Conn.). By way of example, other means for determining and measuring the levels of PA system analytes in a sample include affinity chromatography, ligand binding assays and lectin binding assays. Immunoassays, especially non-radioisotopic enzymatic immunoassays, are preferred. Normal range and normal mean values can be determined for the assay being carried out, as is known and practiced in the art, based on normal (healthy) population samples.

Antibodies directed against the PA system analytes, or antigenic or immunogenic epitopes thereof, i.e., uPA, PAI-1, and the uPA:PAI-1 complex, can be, for example, polyclonal or monoclonal antibodies. Antibodies suitable for use in the assays of the present invention also include chimeric, single chain, and humanized antibodies, as well as Fab, F(ab')$_2$, or Fv fragments, or the product of a phage display library, e.g., an Fab expression library. Various procedures known in the art may be used for the production of such antibodies and antibody fragments. Examples of phage display methods that can be used to make antibodies for use in the present invention include those disclosed in Brinkman et al., 1995, *J. Immol. Methods*, 182:41-50; Ames et al., 1995, *J. Immol. Methods*, 184:177-186; Kettleborough et al., 1994, *Eur. J. Immol.*, 24:952-958; Persic et al., 1997, *Gene*, 187:9-18; Burton et al., 1994, *Advances in Immunology*, 57:191-280; and in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Antibodies generated against the PA system analytes can be obtained by direct injection of an immunogenic uPA, PAI-1, or uPA:PAI-1 preparation into an animal, or by administering all, or a portion, of the analyte polypeptide to an animal, preferably a nonhuman animal. For the preparation of monoclonal antibodies, any technique which provides antibodies produced by continuous cell line cultures can be used. Examples include the hybridoma technique (Kohler and Milstein, 1975, *Nature*, 256:495-497), the trioma technique, the human B-cell hybridoma technique (Kozbor et al., 1983, *Immunol. Today*, 4:72), and the EBV-hybridoma technique to produce human monoclonal antibodies (Cole et al., 1985. *In: Monoclonal Antibodies and Cancer Therapy*, Alan R. Liss, Inc., pp. 77-96). Techniques described for the production of single chain antibodies (U.S. Pat. No. 4,946,778) can be adapted to produce single chain antibodies to the uPA, PAI-1, and/or uPA:PAI-1 PA system analytes. Also, transgenic mice may be used to express humanized antibodies to immunogenic uPA, PAI-1, or uPA:PAI-1 complex.

Methods for producing and screening for anti-PA system analyte-specific antibodies using hybridoma technology are routine and well known in the art. In a nonlimiting example, mice can be immunized with an immunogen, i.e., uPA, PAI-1, or uPA:PAI-1 complex polypeptide or peptide thereof, or with a cell expressing the polypeptide or peptide. Once an immune response is detected, e.g., antibodies specific for the antigen are detected in the sera of immunized mice, the spleen is harvested and splenocytes are isolated. The splenocytes are then fused by well known techniques to any suitable myeloma cells, for example cells from cell line SP2/0 or P3X63-AG8.653 available from the ATCC. Hybridomas are selected and cloned by limiting dilution techniques. The hybridoma clones are then assayed by methods known in the art to determine and select those cells that secrete antibodies capable of binding to a polypeptide of the invention. Ascites fluid, which generally contains high levels of antibodies, can be generated by injecting mice with positive hybridoma clones.

PA system analyte polypeptides comprising one or more immunogenic epitopes of the PA system analytes which elicit an antibody response can be introduced together with a carrier protein, such as an albumin, to a host animal (such as rabbit, mouse, rat, sheep, or goat). Alternatively, if the polypeptide is of sufficient length (e.g., at least about 25 amino acids), the polypeptide can be presented without a carrier. However, immunogenic epitopes comprising as few as 5 to 10 amino acids have been shown to be sufficient to raise antibodies capable of binding to, at the very least, linear epitopes in a denatured polypeptide (e.g., in Western blotting).

The PA system analytes, or peptides thereof, can be used to induce antibodies according to methods well known in the art including, but not limited to, in vivo immunization, in vitro immunization, and phage display methods. See, e.g., Sutcliffe et al., 1983, *Science*, 219:660-666; Wilson et al., 1984, *Cell*, 37:767-778; and Bittle et al., 1985, *J. Gen. Virol.*, 66:2347-2354). If in vivo immunization is used, animals can be immunized with free peptide; however, the anti-peptide antibody titer may be boosted by coupling the peptide to a macromolecular carrier, such as keyhole limpet hemacyanin (KLH), or tetanus toxoid (TT). For instance, peptides containing cysteine residues can be coupled to a carrier using a linker such as maleimidobenzoyl-N-hydroxysuccinimide ester (MBS), while other peptides may be coupled to carriers using a more general linking agent, such as glutaraldehyde.

Antibodies specific for the PA system analytes can be produced by any method known in the art for the synthesis of antibodies, in particular, by chemical synthesis, by intracellular immunization (i.e., intrabody technology), or by recombinant expression techniques. Methods of producing antibodies include, but are not limited to, hybridoma technology, EBV transformation, as well as through the use recombinant DNA technology. Recombinant expression of an antibody, or a fragment, derivative, variant or analog thereof, (e.g., a heavy or light chain of an anti-PA system analyte antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule can be produced by recombinant DNA technology using techniques well known in the art. In vitro recombinant DNA techniques, synthetic techniques, and in vivo genetic recombination methods, which are well known to those skilled in the art, can be used to construct expression vectors containing antibody coding sequences and appropriate transcriptional and translational control signals. Such vectors can include the nucleotide sequence encoding the constant region of the antibody molecule (see, e.g., PCT Publication WO 86/05807; PCT Publication WO 89/01036; and U.S. Pat. No. 5,122,464) and the variable region of the antibody cloned into such a vector for expression of the entire heavy or light chain.

The expression vector is then introduced into a host cell by conventional techniques and the transfected cells are cultured by conventional techniques to produce an anti-PA system analyte antibody. A variety of host expression vector systems can be utilized to express the antibody molecules. Such expression systems represent vehicles by which the coding sequences of interest can be expressed, their encoded products produced and subsequently purified. These systems also represent cells which can, when transformed or transfected with the appropriate nucleotide coding sequences, express an antibody molecule of the invention in situ. Cell expression systems include, but are not limited, to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces* or *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus (CaMV) or tobacco mosaic virus (TMV)), transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as E. coli, and more preferably, eukaryotic cells, especially for the expression of whole recombinant antibody molecules, are used for the expression of a recombinant antibody molecule. For example, mammalian cells such as Chinese hamster ovary (CHO) cells, in conjunction with a vector such as the major intermediate early gene promoter element from human cytomegalovirus, is an effective expression system for antibody production (Foecking et al., 1986, *Gene*, 45:101; Cockett et al., 1990, *Bio-Technology*, 8:2).

Once an anti-PA system analyte antibody has been produced by an animal, chemically synthesized, or recombinantly expressed, it can be purified by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins.

Typically, an ELISA assay initially involves preparing an antibody specific to a given PA system analyte, preferably a monoclonal antibody. In addition, a reporter antibody is used. In some ELISA protocols, the reporter antibody recognizes and binds to the anti-PA analyte-specific monoclonal antibody. To the reporter antibody is attached a detectable reagent such as a radioactive isotope, a fluorescent moiety, a chemiluminescent moiety, or, in an ELISA, an enzyme, such as horseradish peroxidase or alkaline phosphatase.

As is appreciated by those skilled in the art, ELISAs can be performed in a number of assay formats. In one ELISA format, a host sample, e.g., a patient body fluid sample, is incubated on a solid support, e.g., the wells of a microtiter plate, or a polystyrene dish, to which the proteins in the sample can bind. Any free protein binding sites on the dish are then blocked by incubating with a non-specific protein such as bovine serum albumin. The monoclonal antibody is then added to the solid support, e.g., the wells or the dish, and allowed to incubate. During the incubation time, the monoclonal antibodies attach to any PA system analyte polypeptides that have attached to the polystyrene dish. All unbound monoclonal antibody is washed away using an appropriate buffer solution. The reporter antibody, e.g., linked to horseradish peroxidase, is added to the support, thereby resulting in the binding of the reporter antibody to any monoclonal antibody which has bound to the PA system analyte present in the sample. Unattached reporter antibody is then washed away. Peroxidase substrate is added to the support and the amount of color developed in a given time period provides a measurement of the amount of PA system analyte that is present in a given volume of patient sample when compared to a standard curve.

In another ELISA format, as described further below and exemplified herein, antibody specific for a particular analyte is attached to the solid support, i.e., the wells of a microtiter plate or a polystyrene dish, and a sample containing analyte is added to the substrate. Detectable reporter antibodies, which bind to the analyte that has bound to the capture antibodies on the support, are then added, after the appropriate incubations and washings, and analyte-antibody complexes are detected and quantified.

In preferred embodiments, the methods of the present invention involve a sandwich ELISA typically performed using microtiter plates. In a particular embodiment for uPA determination (see, e.g., Examples 1 and 4), the microtiter ELISA employs two monoclonal antibodies to human uPA as the capture reagents. Briefly, the capture antibodies are immobilized on the interior surface of the wells of the microtiter plate. To perform the test, an appropriate volume of serum sample is incubated in the coated wells to allow binding of the antigen, i.e., uPA, in the sample by the capture antibodies. The immobilized antigen is then reacted with uPA detector rabbit antiserum. The amount of detector antibody bound to the antigen is measured by binding it with a goat-anti-rabbit IgG horseradish peroxidase (HRP) conjugate. Color development by incubation with o-phenylenediamine (OPD) substrate enables the quantification of captured uPA. The colored reaction product is quantified by spectrophotometry and reflects the amount of uPA analyte that is present in the plasma sample. A significant change in absorbance indicates a positive result.

In a particular embodiment for PAI-1 determination (see, e.g., Examples 2 and 5), the microtiter ELISA employs a monoclonal antibody directed against human PAI-1 as the capture reagent. Briefly, the capture antibody is immobilized on the interior surface of the wells of the microtiter plate. To perform the test, an appropriate volume of sample, e.g., plasma, is incubated in the coated well to allow binding of the antigen by the capture antibody. The immobilized antigen is then reacted with PAI-1 detector rabbit antiserum. The amount of detector antibody bound to the antigen is measured by binding it with a goat-anti-rabbit IgG horseradish peroxidase (HRP) conjugate. Color development by incubation with o-phenylenediamine (OPD) substrate enables the quantification of captured PAI-1. The colored reaction product is quantified by spectrophotometry and reflects the amount of PAI-1 analyte that is present in the plasma sample.

In a particular embodiment for the determination of uPA:PAI-1 complex (see, e.g., Examples 3 and 5), the microtiter ELISA employs two monoclonal antibodies to human uPA as the capture reagents. Briefly, the capture antibodies are immobilized on the interior surface of the wells of the microtiter plate. To perform the test, an appropriate volume of sample, e.g., plasma, is incubated in the coated wells to allow binding of the antigen by the capture antibodies. The immobilized antigen is then reacted with PAI-1 detector rabbit antiserum. The amount of detector antibody bound to the antigen is measured by binding it with a goat-anti-rabbit IgG alkaline phosphatase conjugate. A substrate solution and an amplifier solution are then added, and once completed, the reaction is quenched by the addition of stop solution. The colored reaction product is quantified by spectrophotometry and reflects the amount of the uPA:PAI-1 protein complex analyte that is present in the plasma sample.

The production of polyclonal and monoclonal antibodies, particularly monoclonal antibodies, that are specific for uPA, PAI-1, or the uPA:PAI-1 complex is performed using techniques and protocols that are conventionally known and practiced in the art, such as described herein, as well as by example in Lars. S. Nielsen, supra. Also, antibodies recognizing the PA system components are commercially available in kit format. (Bayer Diagnostics/Oncogene Science, Cambridge, Mass.; and American Diagnostica, Greenwich, Conn.).

Standards are used to allow accurate, quantitative determinations of the PA system analytes in the samples undergoing analysis. A microtiter plate reader simultaneously measures the absorbance of the colored product in the standard and the sample wells. Correlating the absorbance values of samples with the standards allows the determination of the levels of uPA, PAI-1, or the uPA:PAI-1 complex in the sample. Samples may be assigned a quantitative value of uPA, PAI-1, or uPA:PAI-1 complex, i.e., in picograms per milliliter (pg/ml), or in nanograms per milliliter (ng/ml), of serum or plasma sample.

According to the present invention, a method is provided that permits the assessment and/or monitoring of patients who will be likely to benefit from both traditional and non-traditional treatments and therapies for cancers and neoplastic disease, particularly those cancers and neoplastic diseases that are associated with the activity of the components of the PA system. The present invention thus embraces testing, screening and monitoring of patients undergoing anti-cancer or anti-neoplastic treatments and therapies, for example, those therapies involving small molecule inhibitors of uPA, PAI-1, or the uPA:PAI-1 complex; anti-uPA, anti-PAI-1, or anti-uPA:PAI-1 antibody-based immunotherapies, used alone, in combination with each other, and/or in combination with anti-cancer drugs, anti-neoplastic agents, chemotherapeutics and/or radiation and/or surgery, to treat cancer patients.

An advantage of the present invention is the ability to monitor, or screen over time, those patients who can benefit from one, or several, of the available cancer therapies, and preferably, to monitor patients receiving a particular type of therapy, or a combination therapy, over time to determine how the patient is faring from the treatment(s), if a change, alteration, or cessation of treatment is warranted; if the patient's disease has been reduced, ameliorated, or lessened; or if the patient's disease state or stage has progressed, or become metastatic or invasive. The cancer treatments embraced herein also include surgeries to remove or reduce in size a tumor, or tumor burden, in a patient. Accordingly, the methods of the invention are useful to monitor patient progress and disease status post-surgery.

The identification of the correct patients for a cancer therapy according to this invention can provide an increase in the efficacy of the treatment and can avoid subjecting a patient to unwanted and life-threatening side effects of the therapy. By the same token, the ability to monitor a patient undergoing a course of therapy using the methods of the present invention can determine whether a patient is adequately responding to therapy over time, to determine if dosage or amount or mode of delivery should be altered or adjusted, and to ascertain if a patient is improving during therapy, or is regressing or is entering a more severe or advanced stage of disease, including invasion or metastasis, as discussed further herein.

A method of monitoring according to this invention reflects the serial, or sequential, testing or analysis of a cancer patient by testing or analyzing the patient's body fluid sample over a period of time, such as during the course of treatment or therapy, or during the course of the patient's disease. For instance, in serial testing, the same patient provides a body fluid sample, e.g., serum or plasma, or has sample taken, for the purpose of observing, checking, or examining the levels of uPA, PAI-1, or the complex of uPA:PAI-1 in the patient by measuring the levels of one or more of these analytes during the course of treatment, and/or during the course of the disease, according to the methods of the invention.

Similarly, a patient can be screened over time to assess the levels of one or more of the PA system analytes in a body fluid sample for the purposes of determining the status of his or her disease and/or the efficacy, reaction, and response to cancer or neoplastic disease treatments or therapies that he or she is undergoing. It will be appreciated that one or more pretreatment sample(s) is/are optimally taken from a patient prior to a course of treatment or therapy, or at the start of the treatment or therapy, to assist in the analysis and evaluation of patient progress and/or response at one or more later points in time during the period that the patient is receiving treatment and undergoing clinical and medical evaluation.

In monitoring a patient's uPA, PAI-1 or uPA:PAI-1 complex levels over a period of time, which may be days, weeks, months, and in some cases, years, or various intervals thereof, the patient's body fluid sample, e.g., a serum or plasma sample, is collected at intervals, as determined by the practitioner, such as a physician or clinician, to determine the levels of one or more of the PA system analytes in the cancer patient compared to the respective levels of one or more of these analytes in normal individuals over the course or treatment or disease. For example, patient samples can be taken and monitored every month, every two months, or combinations of one, two, or three month intervals according to the invention. Quarterly, or more frequent monitoring of patient samples, is advisable.

The levels of the one or more PA system analytes found in the patient are compared with the respective levels of the one or more of these PA system analytes in normal individuals, and with the patient's own PA system analyte levels, for example, obtained from prior testing periods, to determine treatment or disease progress or outcome. Accordingly, use of the patient's own PA system analyte levels monitored over time can provide, for comparison purposes, the patient's own values as an internal personal control for long-term monitoring of uPA, PAI-1, and/or uPA:PAI-1 complex levels. As described herein, following a course of treatment or disease, the determination of an increase in one or more of the PA system component levels in the cancer patient over time compared to the respective levels of one or more of these analytes in normal individuals reflects the ability to determine the severity or stage of a patient's cancer, or the progress, or lack thereof, in the course or outcome of a patient's cancer therapy or treatment.

For a variety of cancers, e.g., lung cancer, prostate cancer, ovarian cancer, gastric cancer, colon cancer and breast (mammary) cancer, an increase or elevation in the levels of one or more of uPA, PAI-1, or the uPA:PAI-1 complex analytes in a cancer patient's body fluid sample, e.g., serum or plasma, compared to the respective levels of one or more of these analytes in normal controls following performance of the method of the invention is indicative of disease progression or severity of the cancer. Elevations or increases in the levels of the PA system analytes in cancer patients is determined by comparing the values obtained from analyzing cancer patient samples to the normal control range values. In performing the method of the present invention, any value outside of the normal control range is considered increased or decreased, depending upon the value. The normal range is the normal mean (i.e., average) value plus/minus (±) two standard deviations.

In monitoring a patient over time, a decrease in the levels of one or more of a patient's PA system analytes from increased levels compared to normal range values to levels at or near to the levels of the analytes found in normal individuals is indicative of treatment progress or efficacy, and/or disease improvement, remission, tumor reduction or elimination, and the like. Likewise, in all of the methods described in the embodiments of this invention, a determination of a decrease of one or more of a patient's uPA, PAI-1, or uPA:PAI-1 complex levels from an elevated level to, or approximately to, the respective levels of one or more of these analytes found in normal individuals provides a further aspect of the methods of the invention, in which a patient's improvement, recovery or remission, and/or treatment progress or efficacy, is able to be ascertained over time following performance of the method.

In one embodiment, a cancer patient's sample is analyzed in accordance with the methods of this invention to determine if there is an increase in the serum or plasma levels of one or more of uPA, PAI-1, or the uPA:PAI-1 complex compared with the respective serum or plasma levels of one or more of these PA system analytes found to be the normal range of uPA, PAI-1, and uPA:PAI-1 complex in normal, cancer-free individuals. (Tables 1, 2 and 3). According to the present invention, normal values of the PA system analytes in serum or plasma have been determined to allow a reliable and standardized comparison between the levels of the uPA, PAI-1 and the uPA:PAI-1 complex analytes in normal controls and the respective levels of these analytes in cancer patients.

The normal values for the uPA analyte in serum are presented in Table 1 in accordance with the present invention:

TABLE 1

| Sample Type | Number Tested | Average Normal Value of uPA in Serum | Range of Normal Values of uPA in Serum* |
|---|---|---|---|
| Normal Males | n = 34 | 1064 pg/ml | 579-1549 pg/ml |
| Normal Females | n = 55 | 1124 pg/ml | 469-1778 pg/ml |
| Normal Males + Normal Females | n = 89 | 1192 pg/ml | 459-1924 pg/ml |

*All normal range and cutoff values represent the mean ± two standard deviations (mean ± 2 SD).

The normal values for the PAI-1 analyte in plasma are presented in Table 2 in accordance with the present invention:

TABLE 2

| Sample Type | Number Tested | Average Normal Value of PAI-1 in Plasma | Cutoff Normal Values of PAI-1 in Plasma* |
|---|---|---|---|
| Normal Males | n = 80 | 23.52 ng/ml | >59.38 ng/ml |
| Normal Females | n = 80 | 26.42 ng/ml | >66.61 ng/ml |
| Normal Males + Normal Females | n = 160 | 25.00 ng/ml | >62.71 ng/ml |

*All normal range and cutoff values represent the mean ± two standard deviations (mean ± 2 SD).

The normal values for the complex of uPA:PAI-1 analyte in plasma are presented in Table 3 in accordance with the present invention:

TABLE 3

| Sample Type | Number Tested | Average Normal Value of uPA:PAI-1 Complex in Plasma | Cutoff Normal Values of uPA:PAI-1 Complex in Plasma* |
|---|---|---|---|
| Normal Males | n = 80 | 152.57 pg/ml | >347.21 pg/ml |
| Normal Females | n = 80 | 79.67 pg/ml | >206.63 pg/ml |
| Normal Males + Normal Females | n = 160 | 114.97 pg/ml | >293.25 pg/ml |

*All normal range and cutoff values represent the mean ± two standard deviations (mean ± 2 SD).

Another embodiment of the present invention encompasses a method of monitoring a cancer patient's course of disease, or the efficacy of a cancer patient's treatment or therapy, in which the patient preferably has a cancer that involves the activity of PA system components. Preferably, the patient has a cancer selected from cancer of the breast (mammary), colon, bladder, lung and prostate. The patient's treatment or therapy can involve an anti-plasminogen activation system-specific treatment or therapy, or more traditional therapies, such as hormone therapy, chemotherapeutic drug therapy, radiation, or a combination of any of the foregoing. The method involves measuring levels of one or more of uPA, PAI-1, or the uPA:PAI-1 complex in a body fluid sample of the cancer patient, preferably a serum sample for uPA determination, and a plasma sample for PAI-1 and uPA:PAI-1 complex determination, and determining if the levels of one or more of the PA system analytes in the patient's sample are increased compared to the respective levels of one or more of these analytes in normal controls during the course of disease or cancer treatment. In accordance with the method, an increase in the levels of the PA system analytes in the cancer patient compared to the respective levels of the PA system analytes in normal controls is indicative of an increase in stage, grade, severity or progression of the patient's cancer and/or a lack of efficacy or benefit of the cancer treatment or therapy provided to the patient during a course of treatment, e.g., poor treatment or clinical outcome. Normal levels, including average normal mean values and normal range values, of each of the PA system analytes for comparative purposes in the methods of the present invention are set forth in Tables 1, 2 and 3 herein.

As will be understood by the skilled practitioner in the art, the monitoring method according to this invention is preferably, performed in a serial or sequential fashion, using samples taken from a patient during the course of disease, or a disease treatment regimen, (e.g., after a number of days, weeks, months, or occasionally, years, or various multiples of these intervals) to allow a determination of disease progression or outcome, and/or treatment efficacy or outcome. If the sample is amenable to freezing or cold storage, the samples may be taken from a patient (or normal individual) and stored for a period of time prior to analysis.

In another of its embodiments, the present invention encompasses the determination of the amounts or levels of one or more additional cancer markers in conjunction with the determination of the levels of one or more of uPA, PAI-1, or the uPA:PAI-1 complex in a sample to be analyzed. Nonlimiting examples of additional cancer markers whose levels are suitable for monitoring along with the levels of the PA system analytes in a patient sample for particular cancers as described herein include HER-2/neu, epidermal growth factor receptor (EGFR), complexed PSA (cPSA), p53 autoantibody, the breast cancer marker CA15-3, and the colon cancer marker CA19-9. By combining the determination of the amounts of one or more of these additional cancer markers with a determination of the levels of the PA system analytes compared with the respective normal values of these PA system analytes, the ability to determine and monitor the disease severity of a patient, and/or patient response, and/or disease outcome can be enhanced and extended.

In a particular aspect of this invention, the above method is performed using a serum sample from patients having metastatic breast cancer to ascertain the levels of uPA in the sera of breast cancer patients compared to the levels of uPA in the serum of normal individuals. uPA levels found to be elevated compared to the normal serum level of uPA of 1.75 ng/ml or 1750 pg/ml (mean ±2 SD), (a normal range of serum uPA of 459-1924 pg/ml), were indicative of decreased response to cancer treatment or therapy, a shorter time to progression and a shorter overall survival time, thereby providing the monitorable status of patient disease and/or response to treatment during the course of disease or a cancer or neoplastic disease treatment or therapy regimen. (Example 4).

As another particular aspect of this invention, the method is performed using a plasma sample from patients having various cancers, e.g., colon, prostate, breast, bladder, or lung cancer, to ascertain the levels of either or both PAI-1 and the uPA:PAI-1 complex in the plasma of these cancer patients. (Example 5). For PAI-1, the plasma of patients having each of the different types of cancers showed elevated levels of this PA system analyte compared with the levels of PAI-1 found in normal plasma. PAI-1 level monitoring can also be indicative of cancer progression, e.g., increased stage or grade of cancer. For colon, breast and lung cancers, the plasma levels of PAI-1 were most elevated in the advanced stage cancer patients, compared to the levels of PAI-1 in normal plasma controls, which was determined to have a normal cutoff value of >63 ng/ml.

In accordance with the present invention, a determination of the amount of the uPA:PAI-1 complex in plasma can be particularly beneficial, as it can provide an indication of the amount of active, or actual, proteolysis that may be occurring in conjunction with a patient's cancer, or cancer progression, because uPA and PAI-1 are in their active forms in the uPA:PAI-1 complex. For colon, prostate, breast and lung cancer patients, as exemplified herein, elevated plasma uPA:PAI-1 complex levels compared to the levels of the complex in normal plasma indicate disease and/or disease severity. For example, the plasma of patients having advanced stage colon, breast and lung cancers showed elevated levels of the uPA:PAI-1 complex compared to the levels of the complex in normal plasma control serum, which was determined to have a normal cutoff value of >293 pg/ml.

In another embodiment, the present invention provides a method of monitoring cancer treatment or the clinical response of a cancer patient undergoing cancer treatment for a cancer, particularly a cancer that is associated with activities of components of the plasminogen activation system. The treatment or therapy can involve targeting of components of the plasminogen activation system via small molecules or antibodies. Alternatively, or in addition, the treatment or therapy can involve more traditional cancer therapies, (e.g., anti-cancer drugs, chemotherapeutics, radiation, hormones), or combinations of any of the types of therapies. The method comprises measuring the levels of one or more of the PA system analytes uPA, PAI-1, or the uPA-PAI-1 complex, in a serum or plasma sample of the cancer patient, preferably before, at the start of, and during the course of the patient's cancer treatment, and determining if the cancer patient has increased serum or plasma levels of one or more of the PA system components compared to the respective serum or plasma levels of the PA system components as determined for normal individuals for each type of sample analyzed. Serum samples, or other body fluid samples, are preferably monitored for uPA level determination, while plasma samples are preferably monitored for the determination of the levels of PAI-1 and the uPA:PAI-1 complex.

The outcome of cancer treatment of the patient is determined based upon the measurement of increased serum or plasma uPA, PAI-1, and/or uPA:PAI-1 complex levels in the patient compared to the respective normal serum or plasma levels of these analytes during the course of time that the patient is monitored, where increased levels of one or more of the plasma or serum uPA, PAI-1, or the uPA-PAI-1 complex in cancer patients relative to the respective normal levels of these analytes in normal serum or plasma correlate with poor treatment or clinical outcome. The method further comprises determining the serum or plasma levels of one or more of uPA, PAI-1, or the uPA:PAI-1 complex after a patient has undergone treatment for a length of time that is deemed by the physician or clinician sufficient to allow a showing of efficacy of the cancer treatment and/or patient response, and determining by performance of the method of the invention whether or not the treated patient's uPA, PAI-1, and/or uPA:PAI-1 complex levels have been lowered to, at, or near those of normal individuals. A lowering or decrease in the patient's uPA, PAI-1, and/or uPA:PAI-1 complex levels during or following a course of treatment or therapy relative to the respective levels of these analytes in normal controls indicates progress and/or efficacy of the cancer treatment or therapy.

In another of its aspects, the present invention encompasses a method of monitoring disease severity or progression of a cancer patient. The method comprises measuring levels of one or more of uPA, PAI-1, or the uPA:PAI-1 complex in a serum or plasma sample of the cancer patient and determining if the cancer patient has increased serum or plasma levels of one or more of the uPA, PAI-1, or uPA:PAI-1 complex analytes compared to the respective normal cutoff serum or plasma level values of one or more of these analytes in normal individuals, e.g., males plus females, are provided in Tables 1, 2 and 3 herein. In the method, cancer severity or progression is monitored in the patient based upon elevated or increased levels in the patient's sample compared to the respective normal PA system analyte levels in normal individuals. According to this method, the most severe cancer stage correlates with the most elevated levels of plasma or serum uPA, PAI, or uPA:PAI-1 complex compared to the respective normal control levels of these PA system analytes. Also in accordance with this method, the following normal cutoff values are considered for comparative purposes in the determination of elevated serum or plasma levels in cancer patients: (i) normal uPA serum level is in the range of about 459 pg/ml to about 1924 pg/ml, with a normal mean value of uPA in male serum of about 1064 pg/ml ±2 SD, and a normal mean value of uPA in female serum of about 1124 pg/ml ±2 SD; (ii) the cutoff for normal PAI-1 plasma level is in the range of >62.71 ng/ml, with a normal mean value of PAI-1 in male plasma of >23.52 ng/ml ±2 SD (cutoff >59.38 ng/ml), and a normal mean value of PAI-1 in female plasma of >24.42 ng/ml ±2 SD (cutoff >66.61 ng/ml); and (iii) the cutoff for normal uPA:PAI-1 complex plasma level is in the range of >293.25 pg/ml, with a normal mean value of the uPA:PAI-1 complex in male plasma of >152.57 pg/ml ±2 SD (cutoff >347.21 pg/ml), and a normal mean value of the uPA:PAI-1 complex in female plasma of >79.67 pg/ml ±2 SD (cutoff >206.63 pg/ml).

In yet another of its embodiments, the present invention provides a method of monitoring cancer treatment, or efficacy thereof, in a cancer patient undergoing such treatment. The method involves measuring the serum or plasma levels of one or more of uPA, PAI-1, or the uPA:PAI-1 complex in a cancer patient and determining if the levels of one or more of these PA system analytes in the patient increases during the cancer treatment compared to the respective levels of one or more of the analytes determined in the serum or plasma samples of normal controls, where an elevation or increase in one or more of the uPA, PAI-1, or uPA:PAI-1 complex levels in the cancer patient compared to the respective levels of one or more of these PA system analytes in normal control plasma or serum during the monitoring period indicates one or more of the following: (i) cancer progression; (ii) a more severe stage of the cancer; (iii) lack of response by the patient to the cancer treatment; or (iv) poor outcome or shorter survival time.

In addition, if, during the course of monitoring the levels of one or more of the PA system analytes in the patient undergoing treatment, a change is found in the levels of one or more of these analytes being measured, such that a decrease in the levels of one or more of the PA system analytes is determined, or a decline in the levels of one or more of the PA system analytes resulting in values at or near the respective normal values of one or more of these analytes is determined, after having monitored an increase or elevation in these levels for a period of time during a patient's treatment, an assessment can be made as to one or more of the following events: (i) the patient is progressing well on the treatment, (ii) the treatment is effective; (iii) the patient is responding to the treatment; and/or (iv) the patient's cancer is not progressing or has been ameliorated or eliminated by the treatment.

In accordance with the present invention, such a method of monitoring and assessment of one or more of the uPA, PAI-1, or uPA:PAI-1 complex levels during a patient's course of treatment or therapy, compared with the respective normal level values of one or more of these analytes, can provide the physician or clinician with a determination of a patient's progress, or regression, as the case may be, as a consequence of a particular cancer or anti-neoplastic disease treatment or therapy. Such a determination advantageously allows tailoring of the treatment or therapy to better or more aggressively attack (or treat) a cancer; it also allows altering dosage, mode of administration, modifying the regimen, or combining therapies to achieve a more effective overall treatment and outcome for the individual patient.

This approach provided by the present invention also allows the practitioner to determine whether dosage or mode of administration should be altered, or whether the drug regimen should be modified, for example, by combining therapies or discontinuing therapies, to try to achieve a more effective overall treatment and outcome for the patient. As an example, if it is determined by way of practicing the present invention that a patient has a high likelihood of relapse (due to the monitoring of a continued increase in the levels of one or more of uPA, PAI-1 and/or the uPA:PAI-1 complex compared with the respective normal levels of these PA system analytes over a number of testing times or intervals), the patient can be treated more rigorously, such as by using systemic chemotherapy and/or radiation therapy, or other treatment combinations. Similarly, when the levels of one or more of the PA system analytes monitored by the present methods are determined to decrease over time, i.e., to levels at, or close to, those of normal controls, less aggressive therapies can be decided upon. The ability to select a personalized course of therapy or treatment regimen, i.e., to be able to choose a less aggressive treatment at or close to the start of treatment, or to alter treatment from aggressive to less aggressive at a time prior to the conventional end of a treatment regimen on the basis of the monitoring analysis methods of this invention, can provide less anguish and suffering for the patient on both an emotional and physical level.

Another embodiment of the invention encompasses a method of determining if a cancer patient is a candidate for anti-plasminogen activation system cancer therapy. The method comprises measuring the levels of PAI-1 or uPA:PAI-1 complex in a plasma sample of the cancer patient; determining if the levels of PAI-1 or uPA:PAI-1 complex in the plasma of the cancer patient are elevated compared to the respective levels of PAI-1 or the uPA:PAI-1 complex in the plasma of normal controls; and selecting the patient having elevated plasma PAI-1 or uPA:PAI-complex levels as a candidate for anti-plasminogen activation system therapy, based on the determination of an elevated level of PAI-1 or uPA:PAI-1 complex in the plasma of the cancer patient compared to the plasma level of PAI-1 or uPA:PAI-1 complex in the normal controls. The levels of PAI-1 or uPA:PAI-1 complex in normal individuals are presented in Tables 2 and 3 herein. As a nonlimiting example according to this method, the anti-plasminogen activator system therapy can be a protease inhibitor, such as amidino phenylalanine-type serine protease inhibitor, or a phenylguanidine-based inhibitor, or a uPA receptor antagonist. In addition, the therapy can be administered in combination with at least one biologically active agent, such as one or more of i) drugs; ii) hormones; or iii) synthetic compounds, such as epirubicin.

The above method can also be performed by measuring the levels of uPA in a cancer patient's body fluid sample, preferably serum, to detect an elevation or increase in the uPA level compared with the normal level of uPA detected in healthy control individuals. An increase in uPA levels in the patient is also, or further, indicative of the patient's likelihood to be a good candidate for treatment or therapy targeting components of the PA system. Accordingly, by the practice of this invention, a given patient can be started on a decided upon treatment regimen, monitored throughout the treatment, and undergo alteration of the treatment, or not, depending on the performance of the method in which detection of elevated or non-elevated levels of one or more of the PA system analytes compared to the respective levels in normal individuals determines how a patient's therapy will be most beneficially individualized and controlled over time.

It is to be understood that in all of the embodiments describing the methods according to the present invention, the monitoring of a cancer patient for disease progression or outcome, or for cancer treatment or therapy efficacy or outcome, can include the analysis of a pretreatment sample taken from the patient at a first time point, and can also include the analysis of a patient's samples taken at a second, third, fourth, or subsequent time, during the course of disease or during a cancer or anti-neoplastic treatment or therapy regimen, or a combination of treatment or therapy regimens.

In another embodiment, the present invention encompasses a method of monitoring patient response to cancer therapy or treatment for a patient having metastatic cancer, particularly breast cancer or prostate cancer. The method involves measuring one or more of the following: the level uPA in a body fluid sample of the cancer patient; the level of PAI-1 in a plasma sample of the cancer patient; and/or the level of the uPA:PAI-1 complex in a plasma sample of the cancer patient prior to, or at the start of, cancer therapy or treatment. At various times during the course of treatment, the levels of uPA, PAI-1, and/or the uPA:PAI-1 complex in the patient's samples are respectively examined to determine if the levels of one or more of these PA system analytes in the cancer patient is increased, decreased, or the same as the respective levels of these same analytes in normal control individuals. If, by practice of the method, it is established that the patient having cancer, e.g., metastatic breast cancer, has increased or elevated uPA, PAI-1, and/or uPA:PAI-1 complex levels compared to the levels of one or more of these PA system component analytes in normal controls, one or more of the following can be determined: (i) the patient has ongoing or progressing metastasis; (ii) there is a likelihood of a decreased or poor response to cancer therapy or treatment; (iii) the patient's survival outcome is poor. If a finding of decreased levels, or the same levels, of the PA system analytes are present in the patient's sample compared with the respective levels of these same analytes in normal control individuals during the course of monitoring the patient, a more optimistic assessment of patient progress, response to treatment and therapy, and survival outcome can be concluded.

An especially heartening determination for the patient and the physician or clinician is the observation of a change in the patient's uPA, PAI-1, and/or uPA-PAI-1 complex levels during a patient's course of treatment, i.e., from a finding of elevated levels of uPA, PAI-1, and/or the uPA:PAI-1 complex in pretreatment or early treatment patient samples to a finding in the patient of decreased uPA, PAI-1, and/or uPA:PAI-1 complex levels, or levels of uPA, PAI-1, and/or uPA:PAI-1 complex that are at, or close to, the respective levels of the uPA, PAI-1, and/or uPA:PAI-1 complex analytes determined in normal individuals. Such a finding reflects, among other things, patient improvement from the treatment or therapy, successful treatment outcome, and/or a change to a less serious stage or phase of disease. In the method, for comparative purposes, the normal range of uPA level is 459-1924 pg/ml (average normal cutoff: 1192 pg/ml ±2 SD); the normal range of PAI-1 level is greater than 63 mg/ml (average normal cutoff: 25 ng/ml ±2 SD); and the normal range of the uPA:PAI-1 complex level is greater than 293 pg/ml (average normal cutoff: 115 pg/ml ±2 SD). In addition, the method can be practiced by including a measurement or determination of the levels of one or more oncoprotein markers selected from the group consisting of HER-2/neu, epidermal growth factor receptor (EGFR), complexed PSA (cPSA), CA15-3 breast cancer marker, CA19-9 colon cancer marker, and p53 autoantibody, which can also assist in the determination of patient outcome following treatment, or during the course of disease.

In another of its embodiments, the present invention encompasses the determination of uPA levels in a body fluid sample, e.g., serum, in a patient having pancreatic cancer to assess whether the levels of this PA system analyte are elevated or increased in pancreatic cancer patients compared to uPA levels in normal control individuals, particularly for the purposes of monitoring pancreatic cancer disease course and/or treatment outcome in patients. The finding of an elevation in uPA levels in body fluid, e.g., serum, samples of both male and female patients compared with gender-matched healthy controls allows an assessment of the status of the pancreatic cancer patient's disease over time, and of the progress of a patient undergoing treatment for his or her pancreatic cancer in accordance with the monitoring feature of this invention. (Example 7).

Further, in a manner similar to the other embodiments of this invention, changes in the uPA levels compared with normal levels, and/or compared with the patient's own uPA levels, during the course of monitoring the patient's disease or treatment status, can serve as an indicator of the pancreatic cancer patient's progress, or lack thereof, in disease advancement and/or treatment. More specifically, if, during the course of monitoring the pancreatic cancer patient, the patient's uPA levels decrease so that the uPA levels approximate those of normal controls, such a result can be encouraging by serving to assess a favorable course of disease, or treatment outcome for the patient. Also, the patient's own uPA levels can be assessed relative to each other to determine patient progress and response, or lack thereof, in disease advancement or treatment outcome over time during the monitoring period.

In addition to monitoring the uPA levels in a body fluid sample of pancreatic cancer patients, the co-measurement and determination of the levels of one or more oncoprotein marker analytes can assist in the determination of patient outcome resulting from disease, or patient outcome during the course of disease, or during or following the course of a therapy regimen to treat pancreatic cancer. The co-analysis of other markers is preferably performed using a serum sample from the pancreatic cancer patient. Such other markers include, without limitation, HER-2/neu, epidermal growth factor receptor (EGFR), complexed PSA (cPSA), CA15-3 breast cancer marker, CA 19-9 colon cancer marker, CEA antigen and p53 autoantibody, with HER-2/neu, CEA and CA19-9 markers being preferred. (Example 8). The finding of an increase in one or more of the cancer markers, other than the PA system analyte markers, such as uPA, in a sample from a pancreatic cancer patient can indicate greater severity of disease, or a poorer disease or treatment outcome.

EXAMPLES

The following examples describe specific aspects of the invention to illustrate the invention and provide a description of the present methods for those of skill in the art. The examples should not be construed as limiting the invention, as the examples merely provide specific methodology useful in understanding and practice of the invention and its various aspects.

Example 1

Enzyme Linked Immunoassay (ELISA) to Measure Levels of uPA in a Body Fluid Sample Serum and plasma samples were centrifuged in a tabletop microcentrifuge to remove all flocculent material and/or particulate matter. After centrifugation, the samples were analyzed without further treatment, or were stored at –70° C. for future analysis. The initial concentration of the serum sample examined did not exceed a concentration of 10% (i.e., a 1:10 dilution of sample in sample diluent), (Bayer Diagnostics/Oncogene Science uPA Microtiter ELISA assay kit manual).

The Bayer Diagnostics/Oncogene Science uPA Microtiter ELISA detects 25 pg/ml of uPA analyte in a test sample. The signal of the 25 pg/ml standard is greater than two times the zero (background) signal. In addition, the uPA ELISA is specific for the detection of uPA; for example, no cross-reactivity is detected against tPA and cathepsin D, even at high challenge doses.

Detailed Protocol

The uPA Microtiter ELISA kit (commercially available from Bayer Diagnostics/Oncogene Science, Cambridge, Mass.) used in this Example has removable strips of wells so that the assay can be performed on multiple occasions, and only the number of wells needed are used. A standard curve was included each time that samples were analyzed. The standard curve performed for each separate assay required 12 wells (6 standards run in duplicate). The six standards and the test samples were run in duplicate. For greater accuracy, each sample was tested at more than one concentration. The contents of the uPA Microtiter ELISA assay manual (Bayer Diagnostics/Oncogene Science, Cambridge, Mass.) are hereby incorporated by reference herein in their entirety.

The uPA standards are housed in six separate vials containing lyophilized pro-uPA. Standards levels were calibrated in mass units (picograms per ml) using an immunoaffinity purified pro-uPA preparation. The standards therefore quantify pro-uPA as well as HMW-uPA (both 52 kDa). Low molecular weight uPA (LMW-uPA) is also detected by the assay, but measurement of this form using the standards can overestimate the quantity present. This should not adversely affect most typical measurements of uPA; however, in cases where LMW-uPA is known to be present at a significant level, the detection of LMW-uPA should be considered. The standards vials were reconstituted with 1 ml of high quality deionized water. As provided, standard 6 contained 350 pg/ml pro-uPA; standard 5 contained pro-uPA at 250 pg/ml; standard 4 contained pro-uPA at 150 pg/ml; standard 3 contained pro-uPA at 75 pg/ml; standard 2 contained pro-uPA at 25 pg/ml; and standard 1 contained pro-uPA at 0 pg/ml.

The appropriate number of 8-well strips was selected from the microtiter plate; the remaining unused strips were saved for subsequent use. In some cases, the entire plate was used. A working 1× solution of platewash buffer, as provided in the kit (Bayer Diagnostics/Oncogene Science, Cambridge, Mass.) was prepared by adding one part platewash concentrate to 19 parts of deionized water and mixing well. The total volume required depended on the washing method used, e.g., automatic microplate washer, manual microplate washer, or hand-held syringe. Approximately 1 liter of the wash buffer was needed to prime an automated washer and run one microtiter plate. The platewash buffer was freshly prepared on the day of use and used at room temperature (18-27° C.).

To perform a same-day assay, samples, standards and other kit reagents were warmed to room temperature prior to addition to the microtiter plate wells and starting the assay. The wells of the microtiter plates were precoated with two monoclonal antibodies directed against human uPA as capture reagents. As necessary, samples were diluted in sample diluent containing BSA and 0.1% sodium azide, as provided. (Bayer Diagnostics/Oncogene Science uPA ELISA kit). The standards and diluted samples were gently mixed without foaming and 100 µl were added in duplicate to the wells of the plates. Four wells were set up with the 0 pg/ml standard—two to measure the background absorbance and two for use as the substrate blank wells. The wells were covered with plastic wrap or plate sealer and the samples were incubated at 37° C. for 2 hours.

After the incubation, the plastic wrap or plate sealer was removed, and the wells were washed using 300 µl per well of plate buffer wash in six cycles, as supplied and directed in kit. The plate was washed for three cycles, rotated 180°, and washed for three more cycles. Thereafter, 100 µl of working conjugate were added to all of the wells, except for the substrate blank well which was left empty. The plate was tapped dry on a stack of paper towels.

Next, 100 µl of detector antibody (rabbit anti-uPA antiserum in 0.01 M PBS, pH 7.4, a protein stabilizer and 0.1% sodium azide, as supplied in the uPA ELISA kit, Bayer Diagnostics/Oncogene Science) were added to all of the wells, except for the substrate blank wells. The plates were incubated at 37° C. for 1.5 hours. During the incubation with the detector antibody, working conjugate was prepared by diluting the conjugate concentrate (50× goat anti-rabbit IgG horseradish peroxidase in buffer) at 1:50 in conjugate diluent (0.01 M PBS, pH 7.4, BSA and 0.01% chloroacetamide), per the Bayer Diagnostics/Oncogene Science uPA ELISA kit instructions. The prepared working conjugate was dispensed into a clean reagent reservoir. Following incubation with detector antibody, the microtiter plates (or strips) were washed with platewash and tapped dry on a stack of paper towels.

100 µl of the prepared working conjugate as described above were added to all of the wells, except for the substrate blank wells. The plates were incubated at room temperature (18-27° C.) for 30 minutes. During the incubation with the working conjugate, the substrate was prepared by dissolving substrate tablets (o-phenylenediamine, OPD, tablets) in substrate diluent (0.1 M citrate buffer, pH 5.0 and 0.01% $H_2O_2$) by vortexing vigorously. One substrate tablet was dissolved in 4 ml of substrate diluent to make the working substrate. Once prepared, the working substrate was used within 30 minutes and was not exposed to light.

After the incubation in working conjugate, the microtiter plates (or strips of wells) were again washed with platewash solution and the plates were tapped dry on a stack of paper towels. Thereafter, 100 µl of the working substrate were added to all of the wells, including the substrate blank wells. The microtiter plates were incubated in the dark at room temperature (18-27° C.) for 45 minutes. Stop solution (2.5 N $H_2SO_4$ solution) was then added to each well to stop the enzymatic reaction. Absorbance was read at 490 nm within 30 minutes.

To perform an overnight assay, diluted samples and standards were added in duplicate to the specified wells as described for the same-day assay. Thereafter the microtiter plates were covered and incubated at room temperature (18-27° C.) for 12-18 hours. On the second day, a 1 hour detector incubation time was used; the rest of the same-day protocol as described above was used.

To evaluate the results obtained from the Example 1 uPA ELISA, the absorbance values were averaged for each of the standard and sample dilutions to arrive at the mean absorbance. The concentration of uPA for each sample was interpolated from the standard curve. A variety of microplate reader software packages are available for analysis of microplate data, e.g., SoftmaxPro™ (Molecular Devices Corporation, Sunnyvale, Calif.; and KC4™, BioTek Instruments, Inc. Winooski, Vt.) that simplify the process. A quadratic curve fitting algorithm (second order polynomial) was used. The results for the samples were expressed as pg/ml in the original sample by correcting the value obtained from the standard curve by the dilution factor used in the assay, per the kit manual.

Example 2

Linked Immunoassay (ELISA) to Measure Levels of PAI-1 in Plasma

Plasma samples were centrifuged in a tabletop microcentrifuge to remove all flocculent material and/or particulate matter. Plasma samples were typically diluted 1:50 in sample diluent as described below and in accordance with the instructions accompanying the Bayer Diagnostics/Oncogene Science PAI-1 Microtiter ELISA assay. The contents of the PAI-1 Microtiter ELISA assay manual (Bayer Diagnostics/Oncogene Science, Cambridge, Mass.) are hereby incorporated by reference herein in their entirety.

The Bayer Diagnostics/Oncogene Science PAI-1 Microtiter ELISA detects 0.10 ng/ml of PAI-1 analyte in a test sample. The signal of the 0.10 ng/ml standard is greater than two times the zero (background) signal. In addition, the PAI-1 Microtiter ELISA is capable of quantifying PAI-1 in the active and latent forms, as well as in complex with uPA or tPA. The assay has been tested for cross-reactivity by challenging with PAI-2, tPA and ovalbumin. No cross-reactivity was detected against these proteins at high challenge doses.

Detailed Protocol

The PAI-1 Microtiter ELISA kit (commercially available from Bayer Diagnostics/Oncogene Science, Cambridge, Mass.) used in this Example has removable strips of wells so that the assay can be performed on multiple occasions, and only the number of wells needed are used. A standard curve was included each time samples were analyzed. The standard curve performed for each separate assay requires 12 wells (6 standards run in duplicate). The six standards and the test samples were run in duplicate. For greater accuracy, each sample was tested at more than one concentration.

The PAI-1 standards are housed in six separate vials containing PAI-1. Standards levels were calibrated in nanograms of PAI-1 per ml using highly purified PAI-1. As provided, standard 6 contained 1.5 ng/ml of PAI-1; standard 5 contained PAI-1 at 1.00 ng/ml; standard 4 contained PAI-1 at 0.60 ng/ml; standard 3 contained PAI-1 at 0.30 ng/ml; standard 2 contained PAI-1 at 0.10 ng/ml; and standard 1 contained PAI-1 at 0 ng/ml.

The appropriate number of 8-well strips was selected from the microtiter plate; the remaining unused strips were saved for subsequent use. In some cases, the entire plate was used. A working 1× solution of platewash buffer was prepared by adding one part platewash concentrate to 19 parts of deionized water and mixing well. The total volume required depended on the washing method used, e.g., automatic microplate washer, manual microplate washer, or hand-held syringe. Approximately 1 liter of the wash buffer was needed to prime an automated washer and run one microtiter plate. The platewash buffer was freshly prepared on the day of use and used at room temperature (18-27° C.).

To perform a same-day assay, samples, standards and other kit reagents were warmed to room temperature prior to addition to the microtiter plate wells and starting the assay. The wells of the microtiter plates were precoated with monoclonal antibody directed against human PAI-1 as capture reagent. As necessary, samples were diluted in sample diluent containing BSA and 0.1% sodium azide, as provided. (Bayer Diagnostics/Oncogene Science PAI-1 ELISA kit instructions). The standards and diluted samples were each gently mixed without foaming and 100 µl were added in duplicate to the wells of the plates. Four wells were set up with the 0 ng/ml standard—two to measure the background absorbance and two for use as the substrate blank wells. The wells were covered with plastic wrap or plate sealer and the samples and standards were incubated at room temperature (18-27° C.) for 3 hours.

After the incubation, the plastic wrap or plate sealer was removed, and the wells were washed using 300 µl per well of plate buffer wash in six cycles, as supplied and directed in the kit. The plate was washed for three cycles, rotated 180°, and washed for three more cycles. Thereafter, 100 µl of detector antibody (rabbit anti-PAI-1 antiserum in 0.01 M PBS, pH 7.4, a protein stabilizer and 0.1% sodium azide, as supplied in the PAI-1 Microtiter ELISA kit, Bayer Diagnostics/Oncogene Science) were added to all of the wells, except for the substrate blank wells. The plates were incubated at room temperature (18-27° C.) for 1.5 hours.

During the incubation with the detector antibody, working conjugate was prepared 15-30 minutes prior to use by diluting the conjugate concentrate (50× goat anti-rabbit IgG horseradish peroxidase in buffer) at 1:50 in conjugate diluent (0.01 M PBS, pH 7.4, BSA and 0.01% chloroacetamide), per the Bayer Diagnostics/Oncogene Science PAI-1 Microtiter ELISA kit instructions. The prepared working conjugate was dispensed into a clean reagent reservoir. Following incubation with detector antibody, the microtiter plates (or strips) were washed with platewash.

100 µl of the prepared working conjugate as described above were added to all of the wells, except for the substrate blank wells. The plates were incubated at room temperature (18-27° C.) for 30 minutes. During the incubation with the working conjugate, the substrate was prepared by dissolving substrate tablets (o-phenylenediamine, OPD, tablets) in substrate diluent (0.1 M citrate buffer, pH 5.0, and 0.01% $H_2O_2$) by vortexing vigorously to assure complete solubilization. One substrate tablet was dissolved in 2 ml of substrate diluent to make the working substrate. During resuspension, a dark opaque or foil-covered tube was used to prevent light leakage. Once prepared, the working substrate was used within 30 minutes and was not exposed to light.

After the incubation in working conjugate, the microtiter plates (or strips of wells) were again washed with platewash. Thereafter, 100 µl of the working substrate were added to all of the wells, including the substrate blank wells. The microtiter plates were incubated in the dark at room temperature (18-27° C.) for 45 minutes. Stop solution (2.5 N $H_2SO_4$ solution) was then added to each well to stop the enzymatic reaction. Absorbance was read at 490 nm within 30 minutes. If the plate was not read immediately after the stop solution was added, the plate was kept in the dark at room temperature until the absorbance was read.

To perform an overnight assay, diluted samples and the standards were added in duplicate to the specified wells as described for the same-day assay. Thereafter the microtiter plates were covered and incubated at room temperature (18-27° C.) for 12-18 hours. On the second day, the remainder of the protocol was followed to develop the plates, as described above for the same-day assay.

To evaluate the results obtained from the Example 2 PAI-1 Microtiter ELISA, the absorbance values were averaged for each of the standard and sample dilutions to arrive at the mean absorbance. Using graph paper, the mean absorbance for each standard was plotted on the y-axis versus the concentration of PAI-1 (in ng/ml) on the x-axis. The concentration of PAI-1 was determined for each sample dilution by interpolation from the standard curve. A variety of microplate reader software packages are available for analysis of microplate data, e.g., SoftmaxPro™ (Molecular Devices Corporation, Sunnyvale, Calif.; and KC4™, BioTek Instruments, Inc. Winooski, Vt.) that simplify the process. A quadratic curve fitting algorithm (second order polynomial) was used.

Example 3

Enzyme Linked Immunoassay (ELISA) to Measure Levels of the uPA:PAI-1 Complex in Plasma The Bayer Diagnostics/Oncogene Science Human uPA:PAI-1 Complex Microtiter ELISA detects 5 pg/ml of uPA:PAI-1 complex in a test sample. The signal of the 5 pg/ml standard is significantly higher than the zero (background) signal. In addition, the uPA:PAI-1 complex ELISA assay has been tested for specificity against PAI-2, tPA, ovalbumin, free uPA and free PAI-1 and showed no cross-reactivity against these proteins at high challenge doses.

Detailed Protocol

The uPA:PAI-1 complex Microtiter ELISA kit (commercially available from Bayer Diagnostics/Oncogene Science, Cambridge, Mass.) used in this Example has removable strips of wells so that the assay can be performed on multiple occasions, and only the number of wells needed are used. A standard curve was included each time samples were analyzed. The standard curve performed for each separate assay requires 12 wells (6 standards run in duplicate). The six standards and the test samples were run in duplicate. For greater accuracy, each sample was tested at more than one concentration. The contents of the uPA:PAI-1 complex Microtiter ELISA assay manual (Bayer Diagnostics/Oncogene Science, Cambridge, Mass.) are incorporated by reference herein in their entirety.

The uPA:PAI-1 complex standards are housed in six separate vials containing lyophilized uPA:PAI-1. Standards levels were calibrated in picograms of uPA:PAI-1 complex per ml. The standards were reconstituted with 1 ml of high quality deionized water prior to use. As provided, standard 6 contained 200 pg/ml of uPA:PAI-1 complex; standard 5 contained uPA:PAI-1 complex at 100 pg/ml; standard 4 contained uPA:PAI-1 complex at 40 pg/ml; standard 3 contained uPA:PAI-1 at 10 pg/ml; standard 2 contained uPA:PAI-1 complex at 5 pg/ml; and standard 1 contained uPA:PAI-1 complex at 0 pg/ml.

For the uPA:PAI-1 complex assay, plasma samples were diluted at least 1:10 prior to application to the microtiter plate. Recommended dilutions are 1:10, 1:20, or 1:40; intermediate or higher dilutions can be used to obtain multiple values that fall on the standard curve. Serial or other dilutions were performed in separate tubes and then added directly to the wells of the microtiter plates. Also according to the Bayer Diagnostics/Oncogene Science uPA:PAI-1 complex ELISA manual, p-nitrophenyl p'-guandinobenzoate (NPGB), (0.15 ml of 1000× stock in DMSO) is to be added to plasma samples after collection prior to application to the ELISA plate so as to prevent the de novo formation of uPA:PAI-1 complexes. NPGB is optimally heated at 37° C. for at least 10 minutes, with shaking or repeated tapping, in order to resolubilize the DMSO. The NPGB stock was diluted 1:1000 in the sample prior to performance of the uPA:PAI-1 assay.

The appropriate number of 8-well strips was selected from the microtiter plate; the remaining unused strips were saved for subsequent use. In some cases, the entire plate was used. A working 1× solution of platewash buffer was prepared by adding one part platewash concentrate to 19 parts of deionized water and mixing well. The total volume required depended on the washing method used, e.g., automatic microplate washer, manual microplate washer, or hand-held syringe. Approximately 1 liter of the wash buffer was needed to prime an automated washer and run one microtiter plate. The platewash buffer was freshly prepared on the day of use and used at room temperature (18-27° C.).

To perform a same-day assay, samples, standards and other kit reagents were warmed to room temperature prior to addition to the microtiter plate wells and starting the assay. The microtiter wells were precoated with two anti-human uPA monoclonal antibodies. As necessary, plasma samples were diluted in sample diluent containing BSA and 0.1% sodium azide, as provided. (Bayer Diagnostics/Oncogene Science uPA:PAI-1 complex ELISA kit instructions). The standards and diluted samples were each gently mixed (by inverting) without foaming, and 100 µl were added in duplicate to the wells of the plates. Four wells were set up with the 0 pg/ml standard—two to measure the background absorbance and two for use as the substrate blank wells. The wells were covered with plastic wrap or plate sealer and the samples and standards were incubated at 37° C. for 3 hours.

After the incubation, the plastic wrap or plate sealer was removed, and the wells were washed using 300 µl per well of plate buffer wash in six cycles, as supplied and directed in the kit. The plate was washed for three cycles, rotated 180°, and washed for three more cycles. Thereafter, 100 µl of detector antibody (rabbit anti-PAI-1 antiserum in 0.01 M PBS, pH 7.4, a protein stabilizer, 2% normal mouse serum (NMS) and 0.1% sodium azide, as supplied in the uPA:PAI-1 complex Microtiter ELISA kit, Bayer Diagnostics/Oncogene Science) were added to all of the wells, except for the substrate blank wells. The plates were incubated at 37° C. for 1 hour.

During the incubation with the detector antibody, working conjugate was prepared by diluting the conjugate concentrate (1000× goat anti-rabbit IgG alkaline phosphatase in buffer) in conjugate diluent (0.01 M PBS, pH 7.4, BSA, 2% NMS and 0.01% chloroacetamide), per the Bayer Diagnostics/Oncogene Science uPA:PAI-1 complex Microtiter ELISA kit instructions. Briefly, in a clean reagent reservoir, the conjugate concentrate was first diluted 1:10 in conjugate diluent to make an intermediate conjugate, and then again diluted 1:100 to make the working conjugate. The prepared working conjugate was dispensed into a clean reagent reservoir. Following incubation with detector antibody, the microtiter plates (or strips) were washed with platewash.

100 µl of the prepared working conjugate as described above were added to all of the wells, except for the substrate blank wells. The plates were incubated at 37° C. for 15 minutes. During the incubation with the working conjugate, the substrate was prepared by reconstituting the substrate in substrate diluent, according to the Bayer Diagnostics/Oncogene Science uPA:PAI-1 complex ELISA instruction manual. Amplifier solution (provided in the Bayer Diagnostics/Oncogene Science uPA:PAI-1 complex ELISA kit) was prepared in the same manner. Both the substrate solution and amplifier solution were vortexed vigorously to insure complete solubilization. Once prepared, the working substrate was used within 30 minutes and was not exposed to light.

After the incubation in working conjugate, the microtiter plates (or strips of wells) were again washed with platewash. Thereafter, 50 µl of the working substrate were added to all of the wells, including the substrate blank wells. The microtiter plates were incubated at room temperature (18-27° C.) for 20 minutes. Next, 50 µl of the amplifier were added to all of the wells, including the substrate blank wells. The microtiter plates were incubated at room temperature (18-27° C.) for 15 minutes. Stop solution (1 M phosphoric acid solution) was then added to each well to stop the enzymatic reaction. Absorbance was read at 490 nm within 60 minutes. If the plate was not read immediately after the stop solution was added, the values can deviate from the true readings.

To perform an overnight assay, diluted samples and the standards were added in duplicate to the specified wells as described for the same-day assay. Thereafter the microtiter plates were covered and incubated at room temperature (18-27° C.) for 12-18 hours. On the second day, the remainder of the protocol was followed to develop the plates, as described above for the same-day assay.

To evaluate the results obtained from the Example 3 uPA:PAI-1 complex Microtiter ELISA, the absorbance values were averaged for each of the standard and sample dilutions to arrive at the mean absorbance. Using graph paper, the mean absorbance for each standard was plotted on the y-axis versus the concentration of uPA:PAI-1 complex (in pg/ml) on the x-axis. The concentration of uPA:PAI-1 complex was determined for each sample dilution by interpolation from the standard curve. A variety of microplate reader software packages are available for analysis of microplate data, e.g., SoftmaxPro™ (Molecular Devices Corporation, Sunnyvale, Calif.; and KinetiCalc™, BioTek Instruments, Inc. Winooski, Vt.) that simplify the process. A linear or a quadratic curve fitting algorithm (second order polynomial) was used, depending on whichever yielded a correlation coefficient closer to 1.0. The results for plasma samples were expressed as pg/ml in the original sample by correcting the value obtained from the standard curve for the dilution factor.

Example 4

Serum uPA Monitoring in Patients with Metastatic Breast Cancer

Pretreatment serum was obtained from 242 metastatic breast cancer patients enrolled in a double-blind, controlled, phase III trial of second-line hormonal therapy (Fadrozole versus Megace). For serum preparation, blood was drawn by forearm venipuncture and then centrifuged at 500×g for 10 minutes at room temperature. The serum supernatant was collected, aliquotted and stored at −70° C.

Serum uPA levels were determined using the uPA Microtiter ELISA assay (Bayer Diagnostics/Oncogene Science, Cambridge, Mass.) as described in Example 1. A normal cutoff value of 1.75 ng/ml (mean +2 SD) was obtained from the analysis of the sera of 29 healthy women between the ages of 40-89. Serum uPA levels above this cutoff value were designated as elevated or increased above normal. For example, since 1.75 ng/1 mL was determined to be the upper limit of normal according to the assay herein, any higher value, e.g., 1.76, 1.77, 1.8, 2, 2.1 and the like, is considered to be an increased or elevated value.

Figure 5:
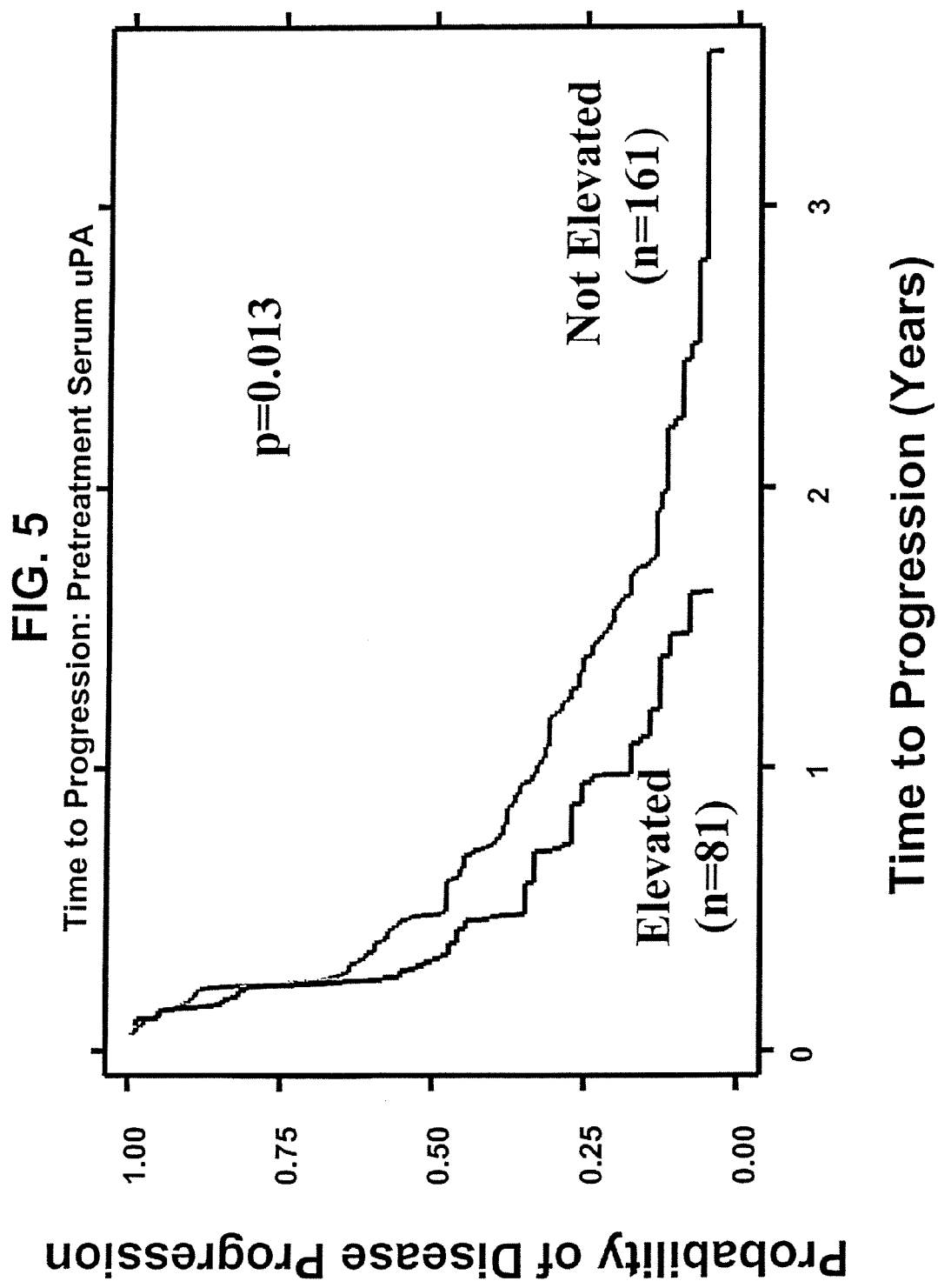
FIG. 5 depicts a graph showing time to progression (TTP) versus probability of disease progression based on the determination of elevated serum uPA levels in breast cancer patients. (Example 4).

The results of the analysis revealed that 33.5% (81/242) of the patients tested had elevated serum uPA levels compared with the normal serum uPA level cutoff in normal individuals. For those patients having an elevated serum uPA level, a trend (p=0.11) toward a decreased response rate (Complete Response (CR)+Partial Response (PR)+Stable Disease) for disease was determined. In addition, the time to disease progression (TTP) was significantly shorter for those patients treated with second-line hormone therapy and having elevated serum uPA levels compared with individuals having normal levels (p=0.013). (FIG. 5). (Table 4).

TABLE 4

Patient response rates as determined by serum uPA status

| Patient Response | Serum uPA Levels Not Elevated | Serum uPA Levels Elevated |
| --- | --- | --- |
| Progressive Disease | 92/161 (57%) | 55/81 (68%) |
| Stable + Partial Response (PR) + Complete Response (CR) | 69/161 (43%) | 26/81 (32%) | p = 0.11

Figure 6:
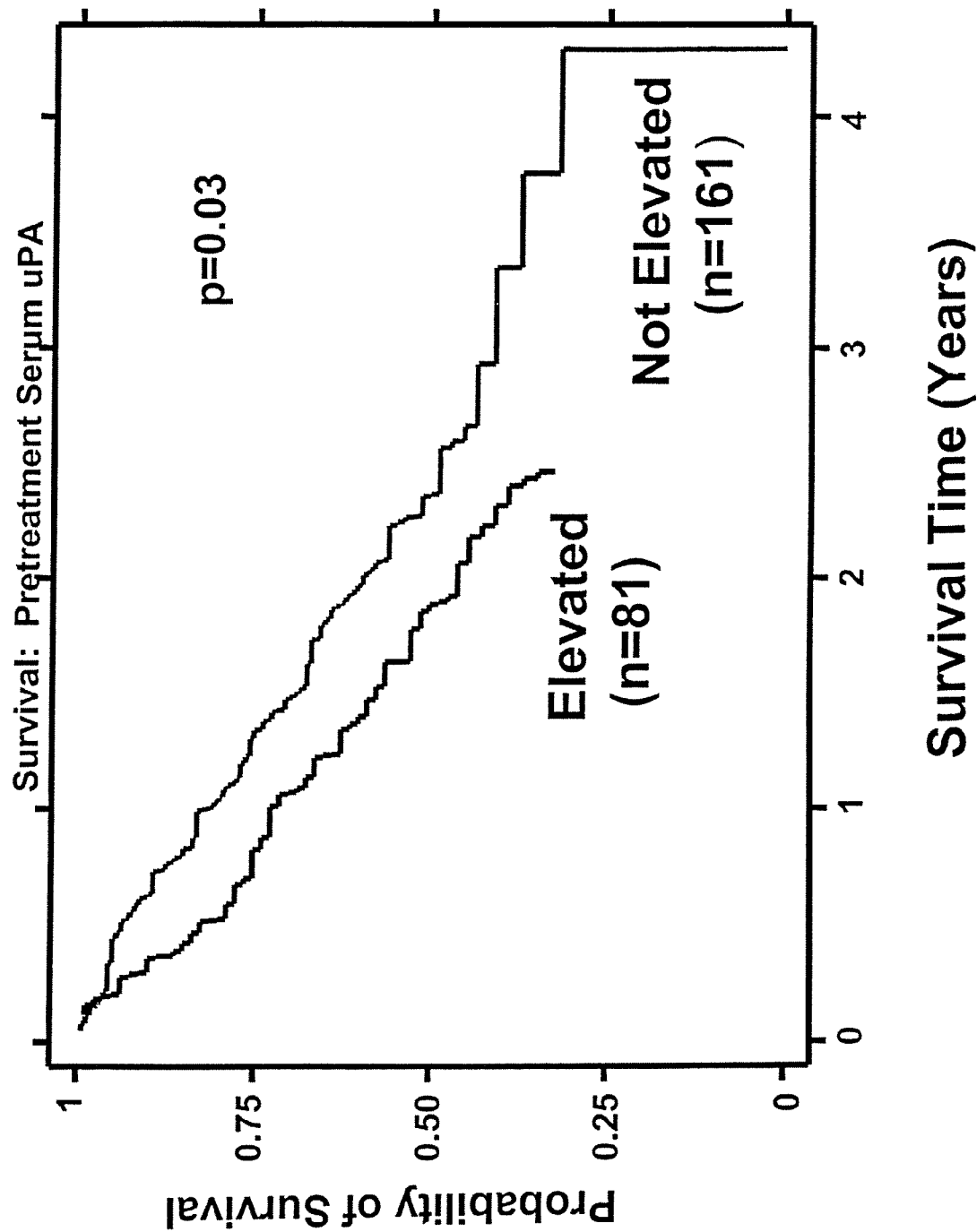
FIG. 6 depicts a graph showing survival time of a cancer patient as a function of probability of survival based on the determination of elevated serum uPA levels in breast cancer patients. (Example 4).

Overall survival was also significantly shorter for patients with elevated serum uPA levels compared with the serum uPA levels in normal individuals. (p=0.03). (FIG. 6). These results demonstrate the value of evaluating patients' serum uPA levels to determine whether the patient's disease is progressing toward a more severe or serious stage and to determine patient outcome. The finding of an increase in serum uPA level compared to normal serum uPA level during the course of monitoring a patient having metastatic breast cancer allowed a determination of one or more of patient treatment efficacy and benefit, TTP, and disease outcome.

Example 5

Microtiter Based ELISA to Examine Plasma Levels of PAI-1 and the Complex of uPA:PAI-1 in Cancer Patient Plasma Samples Active PAI-1 forms an equimolar covalent complex with active uPA, but not with inactive pro-uPA (P. A. Andreasen et al., 1986, *J. Biol. Chem.*, 261:7644-7651). Because both enzymes must be in the active form in order to form complexes, the quantity of uPA:PAI-1 complex found in plasma is determined in this example, as well as the quantity of PAI-1 alone. The detection and measurement of the uPA:PAI-1 complex may be more indicative of active proteolysis that is occurring in vivo via the plasminogen activation system than measurement of either the uPA or the PAI-1 analyte alone.

In this example, normal plasma levels for both PAI-1 and uPA:PAI-1 complexes were established. In addition, plasma samples from a number of cancer types were examined to determine the relative plasma levels of PAI-1 and uPA:PAI-1 complexes in different cancers. The results are particularly useful in light of the advent of therapies molecularly targeted to the plasminogen activation system and its components.

The PAI-1 and uPA:PAI-1 complex ELISA assays employed in this Example are standardized microtiter-based sandwich ELISAs which utilize an endpoint determination of enzymatic color changes. See, Examples 2 and 3 above. The assay run time was approximately six hours for the PAI-1 ELISA and five hours for the uPA:PAI-1 complex ELISA.

Plasma samples from healthy individuals were directly collected in collection tubes coated with EDTA as anticoagulant (Becton-Dickinson, Franklin Lakes, N.J.). Red blood cells were centrifuged to pellet, resulting in plasma supernatant, used as a normal human EDTA plasma sample. The normal human EDTA plasma samples were diluted in ELISA kit sample diluent and then analyzed in either the PAI-1 or the uPA:PAI-1 complex microtiter ELISA assay as described in Examples 2 and 3, respectively. A standard curve with standards tested in duplicate was run in each ELISA. All normal plasma samples were tested in duplicate by at least two different operators. Mean values were obtained for all of the samples tested. A total of 80 normal male and 80 normal female plasmas were tested in order to determine a normal cutoff. The cutoff was defined as the mean value +/−two standard deviations.

Cancer patient plasma was then analyzed in both the PAI-1 and uPA:PAI-1 complex ELISA assays, as described in Examples 2 and 3 above, with samples tested in duplicate by at least two different operators. Test samples were from 50 patients having cancers of the breast, colon, lung, or prostate. Plasma samples from 8 patients having bladder cancer were evaluated. All other experimental parameters were as described for the normal plasma samples.

Figure 2:
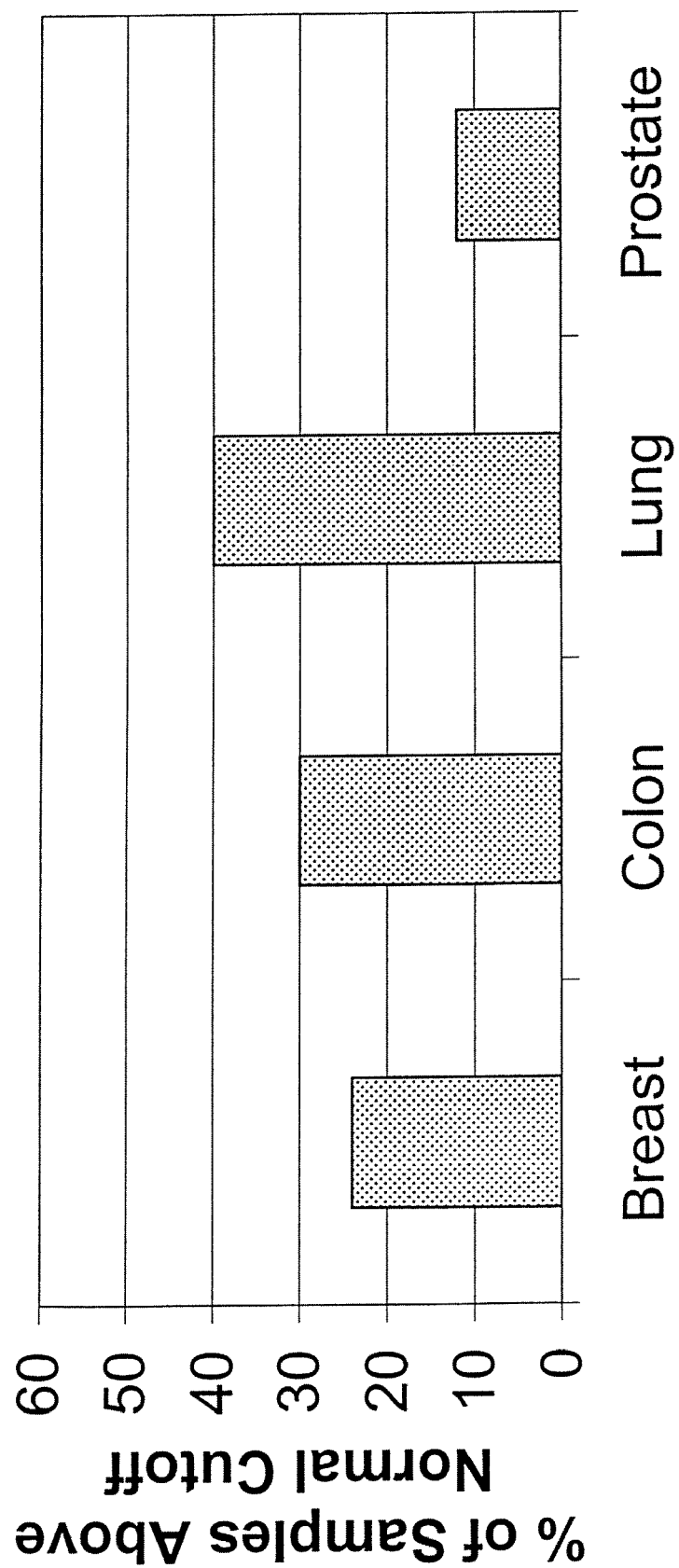
FIG. 2 shows the increases in plasma PAI-1 levels by cancer type, i.e., the percent of patients having plasma PAI-1 levels above the normal cutoff, in patients having breast, colon, lung, or prostate cancers. In this analysis, for breast cancer patients, plasma PAI-1 levels in 24% of the patients were found to be above plasma PAI-1 levels in normal controls; for colon cancer patients, plasma PAI-1 levels in 30% of the patients were found to be above normal plasma PAI-1 levels; for lung cancer patients, plasma PAI-1 levels in 40% of the patients were found to be above normal plasma PAI-1 levels; and for prostate cancer patients, plasma PAI-1 levels in 12% of the patients were found to be above normal plasma PAI-1 levels.
Figure 3:
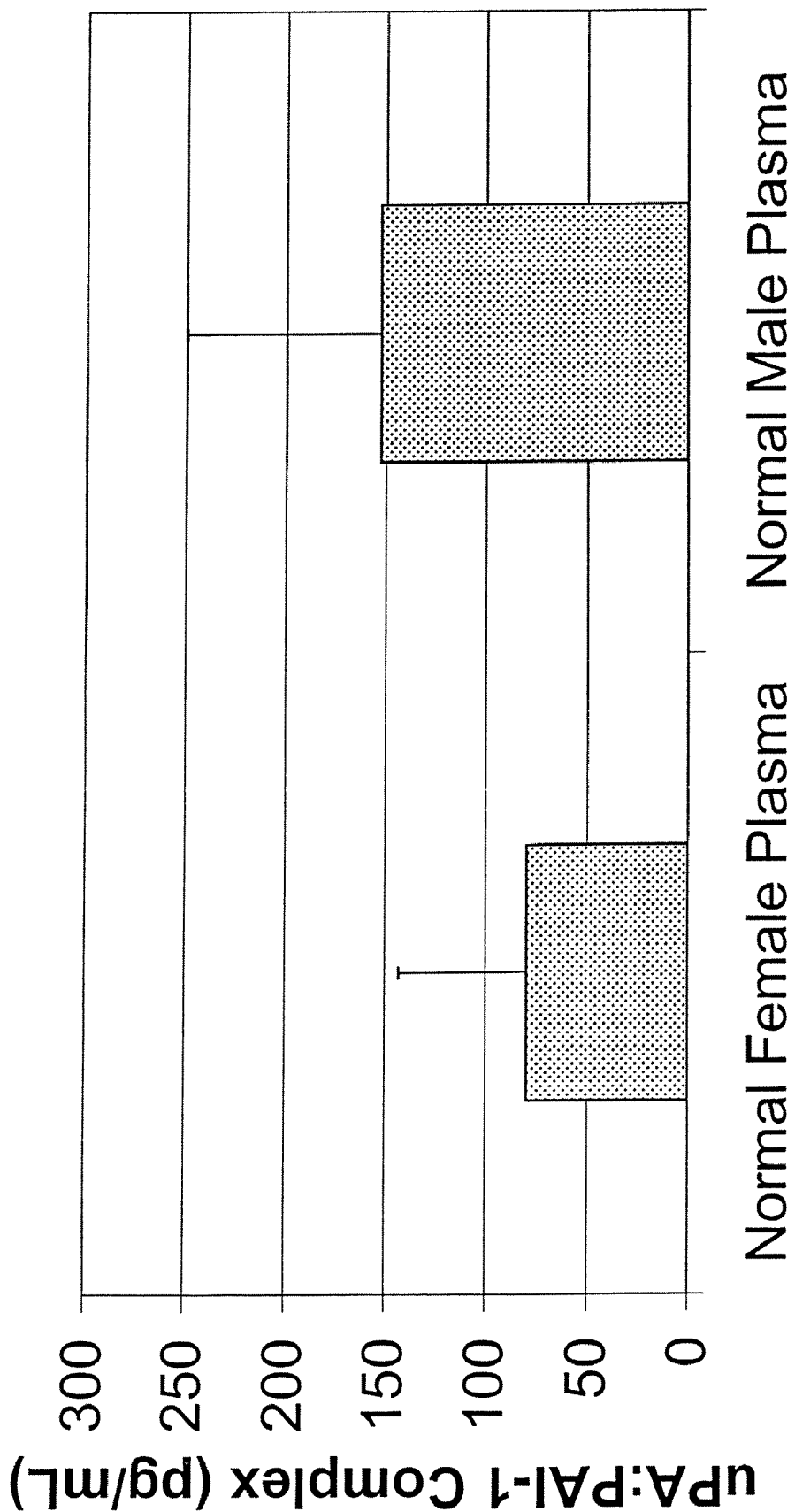
FIG. 3 illustrates the mean uPA:PAI-1 complex levels in normal male and normal female plasma.
Figure 4:
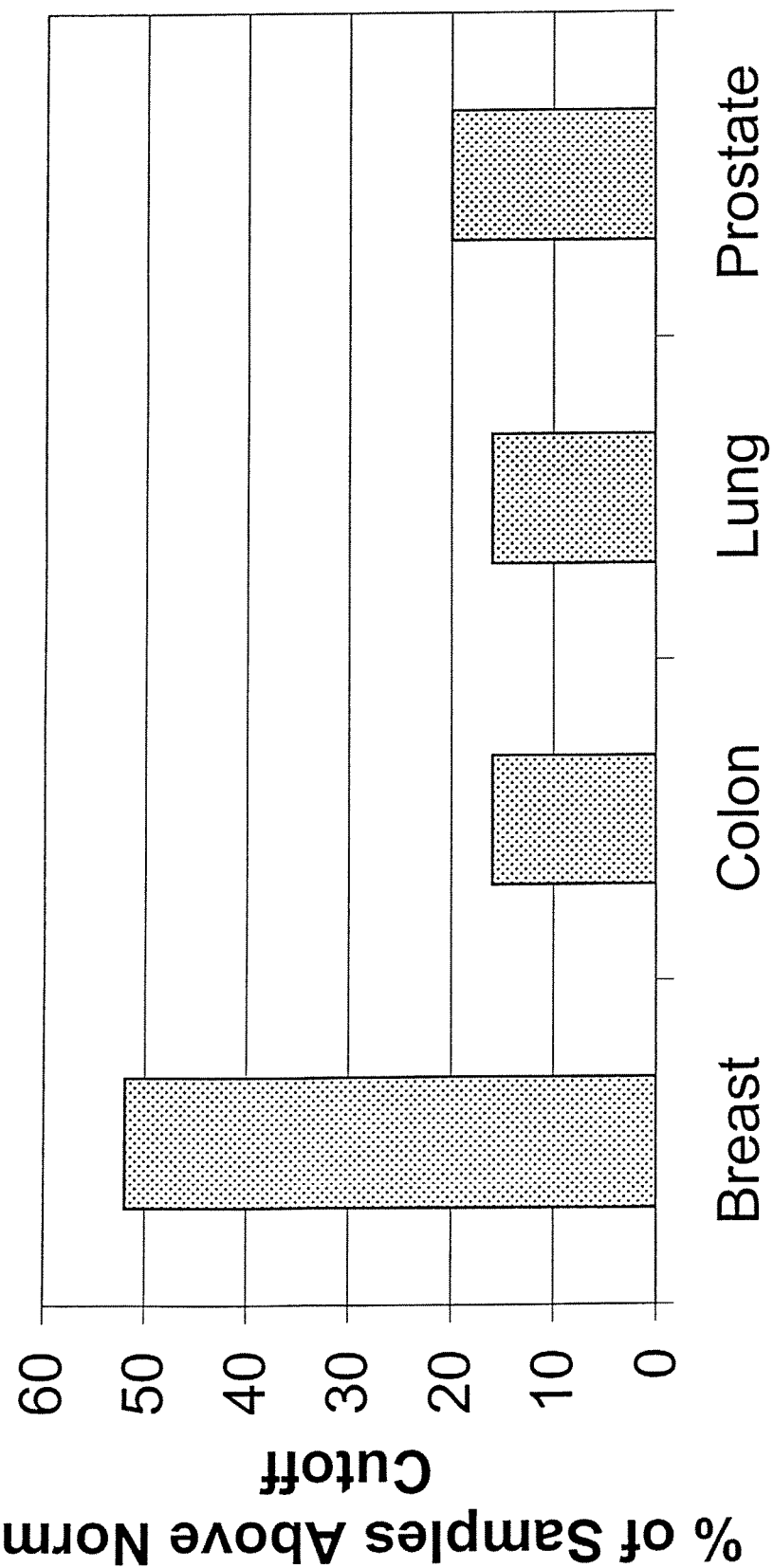
FIG. 4 shows the increases in plasma uPA:PAI-1 complex levels by cancer type, i.e., the percent of patients having plasma uPA:PAI-1 complex levels above the normal cutoff, in patients having breast, colon, lung and prostate cancers. In this analysis, for breast cancer patients, plasma uPA:PAI-1 complex levels in 52% of the patients were found to be above the plasma uPA:PAI-1 complex levels in normal controls; for colon cancer patients, plasma uPA:PAI-1 complex levels in 16% of the patients were found to be above normal plasma uPA:PAI-1 complex levels; for lung cancer patients, plasma uPA:PAI-1 complex levels in 16% of the patients were found to be above normal plasma uPA:PAI-1 complex levels; and for prostate cancer patients, plasma uPA:PAI-1 complex levels in 20% of the patients were found to be above normal plasma uPA:PAI-1 complex levels.

The determination of a normal value was defined as the mean value for the 160 normal plasma samples +/−two standard deviations. The results from the cancer plasma samples were compared to the normal range. Any of the cancer plasma samples that were above the normal range were considered elevated for either PAI-1 or uPA:PAI-1 complexes, and any of the cancer plasma samples that were below the normal range were considered decreased for either PAI-1 or uPA:PAI-1 complexes. Graphical representations of the results were then generated. (FIG. 2).

Colon Cancer Patient Plasma PAI-1 Levels A total of 50 plasma samples from colon cancer patients were analyzed in the PAI-1 microtiter ELISA. Fifteen of the 50 colon cancer plasmas (30%) showed elevated PAI-1 levels when compared with the normal range (63 ng/mL). Of the nine stage IV colon cancer plasmas, all nine (100%) had elevated PAI-1 plasma levels.

Prostate Cancer Patient Plasma PAI-1 Levels A total of 50 prostate cancer plasma samples were analyzed in the PAI-1 microtiter ELISA. Six of the 50 (12%) showed elevated PAI-1 levels when compared with the normal range (63 ng/mL).

Breast Cancer Patient Plasma PAI-1 Levels A total of 50 breast cancer plasma samples were analyzed in the PAI-1 microtiter ELISA. Twelve of the 50 (24%) showed elevated PAI-1 levels when compared with the normal range (63 ng/mL). In stage III breast cancer plasmas, 4/21 (19%) showed PAI-1 levels above the normal range, while in stage IV breast cancer plasmas, 8/29 (28%) showed PAI-1 levels above the normal range.

Lung Cancer Patient Plasma PAI-1 Levels A total of 50 lung cancer plasma samples were analyzed in the PAI-1 microtiter ELISA. Twenty of the 50 (40%) showed elevated PAI-1 levels when compared to the normal range. In stage II lung cancer plasma 2/10 (20%) showed PAI-1 levels above the normal range, in stage III lung cancer plasma 10/32 (31%) showed PAI-1 levels above the normal range and in stage IV lung cancer plasma 5/7 (71%) showed PAI-1 levels above the normal range.

Colon Cancer Patient Plasma uPA:PAI-1 Complex Levels

A total of 49 plasma samples from colon cancer patients were analyzed in the uPA:PAI-1 complex microtiter ELISA. Eight of the 49 colon cancer plasmas (16%) showed elevated uPA:PAI-1 complex levels when compared with the normal range (293 pg/mL). Of the nine stage IV colon cancer plasmas, 6/9 (67%) had elevated uPA:PAI-1 levels. Elevated levels of the uPA:PAI-1 complex compared with normal plasma levels of the uPA:PAI-1 complex were also found in plasma from patients having other stages of colon cancer as follows: 1/16 (6%) of stage C2 colon cancer plasmas had elevated levels of the uPA:PAI-1 complex; 1/1 (100%) of stage III colon cancer plasmas had elevated levels of the uPA:PAI-1 complex; no significant elevation of uPA:PAI-1 complex levels was observed in stage B1 colon cancer (0/2, 0%); stage B2 colon cancer (0/6, 0%); and stage C1 (0/12, 0%); stage D (0/2, 0%).

Prostate Cancer Patient Plasma uPA:PAI-1 Complex Levels

A total of 50 prostate cancer plasma samples were analyzed in the uPA:PAI-1 complex microtiter ELISA. Eight of the 50 (20%) showed elevated uPA:PAI-1 complex levels when compared with the normal range (293 pg/mL).

Breast Cancer Patient Plasma uPA:PAI-1 Complex Levels

A total of 50 breast cancer plasma samples were analyzed in the uPA:PAI-1 complex microtiter ELISA. Twenty-six of the 50 (52%) showed elevated uPA:PAI-1 complex levels when compared with the normal range (293 pg/mL). In stage III breast cancer plasmas, 8/21 (38%) showed uPA:PAI-1 complex levels above the normal range, while in stage IV breast cancer plasmas, 18/29 (62%) showed uPA:PAI-1 complex levels above the normal range.

Lung Cancer Patient Plasma uPA:PAI-1 Complex Levels

A total of 49 lung cancer plasma samples were analyzed in the uPA:PAI-1 complex microtiter ELISA. Eight of the 49 (16%) showed elevated uPA:PAI-1 complex levels when compared with the normal range (293 pg/mL). In stage II lung cancer plasma 0/10 (0%) showed uPA:PAI-1 complex levels above the normal range; in stage III lung cancer plasma 7/32 (22%) showed uPA:PAI-1 complex levels above the normal range; and in stage IV lung cancer plasma 1/7 (14%) showed uPA:PAI-1 complex levels above the normal range.

Bladder Cancer Patient Plasma uPA:PAI-1 Complex Levels

For the bladder cancer patient samples analyzed for levels of the uPA:PAI-1 complex in plasma samples, 25% were found to be elevated.

Example 6

Serial Analysis of uPA Levels in Sera from Prostate Cancer Patients

Serum samples were obtained from 25 prostate cancer patients. Each of the patients had from 4 to 6 serial blood samples drawn, from which the serum component was used. The serum samples were obtained in frozen form and were thawed prior to analysis by ELISA, as described in Example 1, for a determination of the level of uPA over time. The samples were analyzed in a serial fashion on a monthly basis, or every two or three months over a nine to twelve month period of time. Monitoring uPA levels in serum samples from patients over time in accordance with the methods of the present invention provides an advantageous approach to check and examine the patient's response to cancer therapy or treatment over an extended time period.

It will be appreciated that although, as exemplified here, the serum samples were frozen, freshly drawn blood samples can be serially collected from patients over the desired time intervals, and the fresh serum (or plasma) obtained therefrom used equally well for analysis. Table 5 presents representative results of uPA levels determined from 5 prostate cancer patients whose serum samples were serially analyzed at six different time intervals during the monitoring period.

TABLE 5

| Patient/Sample No. | Draw Date | uPA pg/ml |
|---|---|---|
| 3350-1 | April-2000 | 1176 |
| 3350-2 | July-2000 | 1397 |
| 3350-3 | August-2000 | 2537 |
| 3350-4 | October-2000 | 1867 |
| 3350-5 | November-2000 | 1317 |
| 3350-6 | March-2001 | 1035 |
| 3351-1 | June-2000 | 848 |
| 3351-2 | July-2000 | 1193 |
| 3351-3 | August-2000 | 1035 |
| 3351-4 | September-2000 | 1007 |
| 3351-5 | November-2000 | 879 |
| 3351-6 | January-2001 | 1569 |
| 3353-1 | December-1999 | 1445 |
| 3353-2 | February-2000 | 1408 |
| 3353-3 | April-2000 | 1322 |
| 3353-4 | June-2000 | 1220 |
| 3353-5 | August-2000 | 1405 |
| 3353-6 | January-2001 | 701 |
| 3360-1 | June-2000 | 6657 |
| 3360-2 | September-2000 | 7727 |
| 3360-3 | December-2000 | 1739 |
| 3360-4 | February-2001 | 1055 |
| 3360-5 | March-2001 | 1107 |
| 3360-6 | April-2001 | 1896 |
| 3362-1 | March-2000 | 1535 |
| 3362-2 | June-2000 | 1498 |
| 3362-3 | August-2000 | 1073 |
| 3362-4 | September-2000 | 1076 |
| 3362-5 | November-2000 | 451 |
| 3362-6 | February-2001 | 1017 |

Example 7

Serum uPA Levels in Patients with Pancreatic Cancer

In this example, uPA levels were determined in sera samples in a phase III clinical trial of 188 patients with advanced pancreatic cancer. A sandwich ELISA to detect uPA (Bayer Diagnostics/Oncogene Science, Cambridge, Mass.), as described in Example 1, was employed to determined the pretreatment serum uPA levels in 188 pancreatic cancer patients (80 females and 108 males) enrolled in a randomized, double-blind, placebo-controlled phase III trial. A healthy control group of 47 males and 62 females was used to determine control serum levels of uPA. Table 5 summarizes the results.

TABLE 5

| Sample | Serum uPA Levels ng/mL | Normal uPA Cutoff Levels (ng/mL) (mean ± 2 SD) |
|---|---|---|
| Normal Males (n = 47) | 1.15 | 1.74 |
| Normal Females (n = 62) | 1.37 | 1.94 |
| Normal Females Pre-menopausal (n = 47) | 1.39 | |
| Normal Females Post-menopausal (n = 15) | 1.31 | |
| Male Pancreatic Cancer Patients (n = 108) | 2.00 | |
| Female Pancreatic Cancer Patients (n = 80) | 1.80 | |

The results showed that serum uPA levels were significantly higher in female (1.37 ng/ml) compared to male (1.15 ng/ml) healthy control individuals (p=0.0002). Within the female control group, there was no significant difference in serum uPA levels between pre-menopausal women (1.39 ng/ml, n=47) and post-menopausal women (1.31 ng/ml, n=15), (p=0.39). Cutpoint analysis was performed separately using the mean ±2 SD for female (1.94 ng/ml) and male (1.74 ng/ml) controls.

In the pancreatic cancer patients, serum uPA levels were elevated in 28 of 80 (35%) of the female patients, and in 53 of 108 (49%) of the male patients. In addition, the mean serum uPA levels were significantly higher in both female (1.80 ng/ml, p<0.00001) and male (2.00 ng/ml, p<0.00001) pancreatic cancer patients when compared to normal controls. These data demonstrate that serum uPA levels are significantly elevated in both male and female pancreatic cancer patients compared to healthy, gender-matched controls.

Example 8

Serum Levels of the HER-2/neu, CEA and CA19-9 Oncoprotein Markers in Patients with Pancreatic Cancer In this example, the serum levels of the HER-2/neu, carcinoembryonic antigen (CEA) and CA 19-9 oncoprotein markers were determined in samples taken from 195 patients with pancreatic cancer using an ELISA assay to specifically detect the HER-2/neu, CEA and CA 19-9 marker antigens. HER-2/neu levels were quantified using the Bayer Immuno 1® System (Bayer Corporation, Tarrytown, N.Y.) in vitro diagnostic assay kit using a sandwich ELISA format, as described in Bayer Publication No. DA4-1242M00, Clinical Method, December, 2000 (Product No. T01-4189-51). CEA levels were quantified using the Bayer Immuno 1® System in vitro diagnostic assay kit using a sandwich ELISA format, as described in Bayer Publication No. DA4-1205C99, Clinical Method, March, 1999 (Product No. T01-3184-51). CA 19-9 levels were quantified using the Bayer Immuno 1® System in vitro diagnostic assay kit using a sandwich ELISA format, as described in Bayer Publication No. DA4-1212K95, Clinical Method, October, 1995 (Product No. T01-3561-51).

The values obtained for these markers in the pancreatic cancer patients' serum are presented in Table 6. For comparison with normal control levels of the respective markers, the normal cutoff for serum levels of HER-2/neu is 15 ng/1 mL, as quantified using the HER-2/neu ELISA assay kit (Bayer Diagnostics/Oncogene Science, Cambridge, Mass.). It is to be understood that similar results are obtained using both the Bayer Diagnostics/Oncogene Science and the Bayer/Technicon Immuno® System sandwich ELISA immunoassay platforms.

The accepted normal range of CEA in the serum of non-smokers is typically <2.5 to 4.0 ng/mL, and <10 ng/mL in the serum of smokers. (*Methods in Clinical Chemistry*, Eds. A. J. Pesce and L. A. Kaplan, The C.V. Mosby Company, Washington, D.C., Chpt. on CEA by A.H. Rule, pp 702-713). The normal cutoff in serum for CA 19-9 is typically 37.0 U/mL. (B. C. Del Villano et al., 1983, *Clin. Chem.*, 29:549-552; and R. I. Ritts Jr. et al., 1984, *Int. J. Cancer*, 33:339-345). An observation of the values listed in Table 6 shows that 21/195 (11%) of the pancreatic cancer patients have elevated serum HER-2/neu levels compared to the normal control value of HER-2/neu in serum; 111/195 (57%) of the pancreatic cancer patients are seen to have elevated CEA levels compared to the normal control range for nonsmokers, while 71/195 (36%) of the pancreatic cancer patients have elevated CEA levels compared to the normal control range for smokers; and 162/195 (83%) of the pancreatic cancer patients are seen to have elevated CA 19-9 levels compared to the normal control cutoff value.

TABLE 6

Serum Levels of the HER-2/neu, CEA and CA 19-9 Oncoprotein Markers

| Sample No. | HER-2/neu (ng/mL) | CEA (ng/mL) | CA 19-9 U/mL |
|---|---|---|---|
| 20045941 | 10.01 | 5.3 | >240 |
| 20050734 | 9.81 | 8.9 | >240 |
| 20051342 | 19.18 | 2.9 | 206.3 |
| 20088733 | 9.70 | 1.3 | 45.2 |
| 20091821 | 11.13 | 0.5 | >240 |
| 20092086 | 15.97 | 19.4 | >240 |
| 20101503 | 8.29 | >100 | >240 |
| 20104573 | 9.95 | 2.1 | 17.1 |
| 20105380 | 8.21 | 4.9 | >240 |
| 20105516 | 17.50 | 24.5 | >240 |
| 20105517 | 12.49 | >100 | >240 |
| 20110061 | 9.67 | >100 | >240 |
| 20110514 | 6.88 | 6.0 | >240 |
| 20111214 | 11.07 | 1.9 | >240 |
| 20111334 | 10.04 | 13.4 | >240 |
| 20111445 | 11.28 | 8.5 | >240 |
| 20111820 | 17.84 | 6.3 | >240 |
| 20111970 | 6.04 | 0.6 | 212.8 |
| 20112105 | 23.28 | 49.5 | 3.1 |
| 20114568 | 10.21 | 55.9 | >240 |
| 20114784 | 10.00 | 1.8 | >240 |
| 20115323 | 8.15 | >100 | >240 |
| 20115331 | 9.45 | 69.7 | >240 |
| 20115559 | 9.74 | 1.5 | 131.1 |
| 20115882 | 12.50 | >100 | >240 |
| 20118172 | 7.24 | 42.6 | 150.9 |
| 20118862 | 15.09 | 13.4 | >240 |
| 20119233 | 8.11 | 6.9 | 139.4 |
| 20119846 | 12.11 | 16.1 | >240 |
| 20120147 | 15.48 | 2.7 | 111.0 |
| 20121657 | 8.28 | 3.3 | >240 |
| 20121927 | 19.74 | >100 | >240 |
| 20122029 | 9.00 | 1.5 | >240 |

TABLE 6-continued

Serum Levels of the HER-2/neu, CEA and CA 19-9 Oncoprotein Markers

| Sample No. | HER-2/neu (ng/mL) | CEA (ng/mL) | CA 19-9 U/mL |
|---|---|---|---|
| 20125601 | 12.48 | 98.7 | >240 |
| 20126517 | 12.10 | 49.7 | 0.1 |
| 20126762 | 7.33 | 20.3 | >240 |
| 20127099 | 11.16 | 6.9 | >240 |
| 20127404 | 11.41 | >100 | >240 |
| 20127548 | 15.27 | 7.9 | 6.6 |
| 20128655 | 13.55 | 21.8 | >240 |
| 20130641 | 9.44 | 2.3 | >240 |
| 20130862 | 21.49 | >100 | >240 |
| 20131082 | 10.21 | 0.3 | 4.9 |
| 20131185 | 11.63 | 2.1 | >240 |
| 20131562 | 7.01 | >100 | >240 |
| 20132765 | 13.88 | 15.5 | >240 |
| 20133718 | 8.94 | 2.8 | 33.6 |
| 20134279 | 13.68 | 18.3 | >240 |
| 20134682 | 8.79 | 2.6 | >240 |
| 20135297 | 23.54 | >100 | >240 |
| 20135456 | 9.58 | 5.2 | >240 |
| 20136960 | 18.48 | 17.7 | >240 |
| 20137399 | 11.28 | 2.2 | 123.5 |
| 20137672 | 10.90 | 1.6 | >240 |
| 20140046 | 12.30 | 2.3 | 23.1 |
| 20140121 | 8.35 | >100 | >240 |
| 20140185 | 8.87 | 2.2 | >240 |
| 20140500 | 8.04 | 1.1 | 5.7 |
| 20140845 | 8.10 | 4.4 | >240 |
| 20141310 | 7.76 | 3.0 | >240 |
| 20142492 | 13.77 | >100 | 5.4 |
| 20144108 | 10.55 | 89.5 | >240 |
| 20144431 | 11.06 | >100 | >240 |
| 20144477 | 12.10 | 6.0 | >240 |
| 20145683 | 9.45 | 6.3 | >240 |
| 20146218 | 11.15 | 1.9 | 65.1 |
| 20146808 | 13.58 | 4.9 | 35.0 |
| 20147388 | 7.65 | 6.1 | 0.2 |
| 20147389 | 9.81 | 40.3 | >240 |
| 20147574 | 14.24 | 16.1 | >240 |
| 20147628 | 25.56 | 5.0 | >240 |
| 20147630 | 11.51 | 1.7 | >240 |
| 20147720 | 7.43 | 1.6 | 0.1 |
| 20147817 | 16.38 | 6.6 | >240 |
| 20149022 | 11.85 | 3.5 | 3.0 |
| 20149167 | 8.54 | 1.6 | >240 |
| 20149386 | 10.33 | 10.5 | >240 |
| 20150245 | 12.95 | 68.6 | >240 |
| 20150467 | 7.57 | 0.8 | 74.0 |
| 20150862 | 7.17 | 58.4 | >240 |
| 20151928 | 10.55 | >100 | 2.0 |
| 20152393 | 9.50 | 1.8 | 95.5 |
| 20152574 | 12.38 | 4.3 | >240 |
| 20152664 | 9.82 | 1.3 | >240 |
| 20152671 | 9.23 | 2.2 | >240 |
| 20152674 | 10.16 | 5.3 | 212.4 |
| 20153322 | 7.56 | 0.7 | >240 |
| 20153865 | 7.39 | 0.8 | >240 |
| 20153936 | 6.07 | 0.6 | 64.2 |
| 20153970 | 8.76 | 81.6 | >240 |
| 20155381 | 12.92 | 0.5 | >240 |
| 20155604 | 14.67 | 3.7 | >240 |
| 20156018 | 8.12 | 4.1 | >240 |
| 20156495 | 10.96 | 2.1 | 2.1 |
| 20156809 | 10.29 | 4.3 | >240 |
| 20157242 | 7.95 | 1.9 | >240 |
| 20157365 | 16.27 | 22.9 | 35.2 |
| 20157372 | 5.72 | 21.6 | >240 |
| 20157845 | 8.57 | 41.7 | 142.8 |
| 20158568 | 9.43 | 10.9 | >240 |
| 20158997 | 10.18 | 1.5 | >240 |
| 20159156 | 13.31 | 1.3 | 14.7 |
| 20161316 | 7.09 | 1.8 | >240 |
| 20161426 | 8.57 | 5.3 | 159.6 |
| 20162000 | 9.19 | 40.7 | >240 |
| 20162270 | 14.15 | >100 | 134.1 |
| 20162733 | 9.34 | 10.4 | >240 |
| 20163253 | 8.00 | 0.4 | 4.2 |
| 20163333 | 7.81 | 2.0 | 1.9 |
| 20163351 | 16.09 | 14.4 | >240 |
| 20163554 | 10.55 | 57.5 | >240 |
| 20163557 | 7.29 | 2.1 | 134.6 |
| 20163562 | 11.61 | 5.5 | >240 |
| 20163594 | 10.31 | 2.8 | 45.2 |
| 20163631 | 8.37 | 1.1 | 223.5 |
| 20163671 | 11.51 | 0.7 | 213.5 |
| 20164080 | 7.65 | 1.2 | 0.3 |
| 20164102 | 9.78 | 53.1 | >240 |
| 20164443 | 14.17 | 88.4 | >240 |
| 20164445 | 23.57 | 5.6 | >240 |
| 20164467 | 17.27 | 1.4 | >240 |
| 20164649 | 12.30 | 44.3 | >240 |
| 20164651 | 16.48 | 18.8 | 2.0 |
| 20165793 | 14.58 | 2.0 | 25.7 |
| 20165804 | 19.62 | 0.7 | 96.0 |
| 20166286 | 15.13 | 9.5 | 0.9 |
| 20166724 | 10.14 | 16.6 | >240 |
| 20167115 | 12.62 | 15.7 | >240 |
| 20167274 | 9.45 | 0.7 | 10.2 |
| 20167318 | 8.87 | 0.5 | 1.4 |
| 20167356 | 9.58 | 1.6 | >240 |
| 20167860 | 9.74 | 2.9 | >240 |
| 20168213 | 13.80 | >100 | >240 |
| 20168615 | 8.06 | 2.1 | >240 |
| 20168808 | 10.82 | 55.6 | >240 |
| 20169306 | 13.33 | 1.3 | >240 |
| 20169306 | 13.52 | 1.3 | >240 |
| 20169451 | 11.10 | 14.0 | >240 |
| 20169453 | 10.68 | 2.5 | >240 |
| 20169453 | 11.36 | 2.3 | >240 |
| 20169854 | 9.88 | 40.9 | >240 |
| 20169962 | 8.57 | 4.7 | >240 |
| 20170019 | 13.82 | 2.1 | >240 |
| 20170084 | 5.96 | 3.0 | >240 |
| 20170101 | 16.86 | 5.5 | >240 |
| 20170621 | 6.13 | >100 | >240 |
| 20170960 | 9.47 | 0.9 | 1.1 |
| 20171007 | 10.53 | 9.2 | 197.7 |
| 20171008 | 11.62 | 2.7 | >240 |
| 20171309 | 6.45 | 11.3 | 13.3 |
| 20171458 | 10.56 | 0.9 | 8.9 |
| 20171818 | 8.31 | 2.2 | >240 |
| 20172065 | 12.08 | >100 | >240 |
| 20172090 | 12.56 | 3.7 | >240 |
| 20172225 | 12.16 | 26.2 | >240 |
| 20172226 | 9.16 | 0.7 | >240 |
| 20172435 | 9.01 | 2.7 | >240 |
| 20172626 | 7.30 | 5.2 | >240 |
| 20172628 | 10.64 | 4.7 | >240 |
| 20172879 | 10.45 | 8.2 | >240 |
| 20173049 | 9.27 | 2.3 | >240 |
| 20173212 | 9.31 | 5.0 | >240 |
| 20173648 | 12.15 | 81.6 | >240 |
| 20173676 | 10.94 | 19.3 | >240 |
| 20174230 | 10.42 | 2.1 | 155.0 |
| 20174434 | 8.35 | 3.2 | >240 |
| 20174435 | 9.85 | 2.0 | >240 |
| 20174674 | 9.90 | >100 | >240 |
| 20175331 | 9.75 | 6.3 | >240 |
| 20175631 | 7.00 | 56.5 | 57.7 |
| 20176100 | 14.40 | >100 | >240 |
| 20176156 | 8.91 | 4.9 | 215.1 |
| 20176650 | 7.23 | 9.9 | 11.7 |
| 20176710 | 11.99 | 7.5 | >240 |
| 20176751 | 6.02 | 64.1 | >240 |
| 20176865 | 9.33 | 17.2 | >240 |
| 20177134 | 9.85 | 0.6 | >240 |
| 20177232 | 9.00 | 2.4 | 192.8 |
| 20177445 | 7.91 | 3.7 | 4.3 |

TABLE 6-continued

Serum Levels of the HER-2/neu, CEA and CA 19-9 Oncoprotein Markers

| Sample No. | HER-2/neu (ng/mL) | CEA (ng/mL) | CA 19-9 U/mL |
|---|---|---|---|
| 20177637 | 8.88 | 1.2 | 201.8 |
| 20178434 | 9.85 | 2.2 | 215.7 |
| 20178826 | 14.63 | >100 | >240 |
| 20178953 | 6.44 | 1.0 | >240 |
| 20178962 | 8.49 | 1.6 | >240 |
| 20179496 | 8.38 | 1.2 | >240 |
| 20180023 | 9.50 | 4.9 | 20.2 |
| 20180795 | 11.42 | 2.3 | 26.2 |
| 20181224 | 13.49 | 1.4 | 51.5 |
| 20181962 | 9.33 | 6.6 | >240 |
| 20182177 | 9.30 | 10.0 | >240 |
| 20182554 | 11.66 | >100 | >240 |
| 20182794 | 14.09 | 37.3 | 237.9 |
| 20183766 | 6.51 | 18.8 | 9.8 |
| 20183902 | 7.98 | 2.8 | >240 |
| 20185847 | 11.05 | >100 | >240 |

The contents of all issued and granted patents, patent applications, published PCT and U.S. applications, articles, books, references, reference and instruction manuals, and abstracts as referenced or cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of monitoring cancer progression, or the efficacy of cancer treatment or therapy, in a cancer patient, comprising:
    (a) measuring the levels of one or more of the following plasminogen activator (uPA) system components in a body fluid sample from the cancer patient prior to, or at the start of, cancer treatment or therapy: (i) uPA in a serum sample, (ii) PAI-1 in a plasma sample; and (iii) uPA:PAI-1 complex in a plasma sample;
    (b) determining if the sample levels of one or more of the uPA, PAI-1, or uPA:PAI-1 complex in the cancer patient is increased compared to normal levels of each of the respective plasminogen activator system components in normal controls to obtain a first value for the PA system analytes in the patient;
    (c) measuring the levels of one or more of (i) uPA in a serum sample of the cancer patient; (ii) PAI-1 in a plasma sample of the cancer patient; or (iii) the uPA:PAI-1 complex in a plasma sample of the cancer patient during and/or following a course of cancer treatment or therapy;
    (d) determining if the patient's sample levels of one or more of the uPA, system components is increased compared to the normal levels of each of the respective plasminogen activator system components in normal controls during and/or following the course of cancer treatment or therapy; and
    (e) establishing that the cancer treatment or therapy is or is not effective; wherein an increase or elevation in the cancer patient's sample levels of one or more of the uPA, PAI-1 or uPA:PAI-1 complex during or following the cancer treatment or therapy compared with the levels of one or more of the uPA, PAI-1 or uPA:PAI-1 complex in normal controls and relative to the first value of (a) indicates that the cancer treatment or therapy is not effective or that the patient is not responding to the treatment or therapy; and further wherein a decrease in the sample levels of one or more of the uPA, PAI-1 or uPA:PAI-1 complex during or following the cancer treatment or therapy compared with the levels of one or more of the uPA, PAI-1 or uPA:PAI-1 complex in normal controls and compared to the first value of (a) indicates effective treatment or therapy, or a favorable response by the cancer patient;
    wherein the normal serum level of uPA is a normal control value of 1924 pg/ml;
    wherein the normal plasma level of PAI-1 is a normal control value of 63 ng/ml; and
    wherein the normal plasma level of uPA:PAI-1 complex is a normal control value of 293 pg/ml.

2. The method according to claim 1, wherein the cancer is a solid tumor cancer.

3. The method according to claim 2, wherein the solid tumor cancer is selected from skin, lung, trachea, breast (mammary), prostate, cervix, ovary, vulva, vagina, endometrium, bladder; pancreas, gall bladder, thyroid, esophagus, head and neck, brain, kidney, liver, stomach, rectum, or colon cancer.

4. The method according to claim 1, wherein the cancer is breast cancer, pancreatic cancer, or prostate cancer.

5. A method of monitoring cancer treatment, or efficacy thereof, in a cancer patient undergoing such treatment, comprising:
    (a) measuring levels of a complex of plasminogen activator (uPA) and uPA inhibitor PAI-1 (uPA:PAI-1 complex) in a plasma sample of the cancer patient; and
    (b) determining if the plasma levels of the uPA:PAI-1 complex increase during the cancer treatment compared to the plasma levels of the uPA:PAI-1 complex in normal controls, which is greater than about 293 pg/ml; wherein an increase in the plasma levels of the uPA:PAI-1 complex in the cancer patient compared to the plasma levels of the complex in normal controls during the monitoring period indicates one or more of the following: (i) cancer progression, (ii) a more severe stage of the cancer, or (iii) lack of response by the patient to the cancer treatment.

6. The method according to claim 5, wherein the cancer patient has a solid tumor cancer.

7. The method according to claim 5, wherein the cancer patient has a cancer selected from skin, lung, trachea, breast (mammary), prostate, cervix, ovary, vulva, vagina, endometrium, bladder; pancreas, gall bladder, thyroid, esophagus, head and neck, brain, kidney, liver, stomach, rectum, or colon cancer.

8. The method according to claim 5, wherein the plasma uPA:PAI-1 complex levels are determined by an enzyme linked immunosorbent assay (ELISA).

9. A method of monitoring cancer treatment, or efficacy thereof, in a cancer patient undergoing such treatment, comprising:
    (a) measuring levels of a complex of plasminogen activator inhibitor-1 (PAI-1) in a plasma sample of the cancer patient; and
    (b) determining if the plasma levels of PAI-1 increase during the cancer treatment compared to the plasma levels of PAI-1 in normal controls, which is greater than about 63 ng/ml; wherein an increase in the plasma levels of PAI-1 in the cancer patient compared with the plasma levels of PAI-1 in normal controls during the monitoring period indicates one or more of the following: (i) cancer progression, (ii) a more severe stage of the cancer, or (iii) lack of response by the patient to the cancer treatment.

10. The method according to claim 9, wherein the cancer patient has a solid tumor cancer.

11. The method according to claim 9, wherein the cancer patients have a cancer selected from skin, lung, trachea, breast (mammary), prostate, cervix, ovary, vulva, vagina, endometrium, bladder; pancreas, gall bladder, thyroid, esophagus, head and neck, brain, kidney, liver, stomach, rectum, or colon cancer.

12. The method according to claim 9, wherein the plasma PAI-1 levels are determined by an enzyme linked immunosorbent assay (ELISA).

13. A method of monitoring patient response to cancer therapy or treatment for a patient having metastatic cancer, comprising:
(a) measuring levels of plasminogen activator (uPA) in a serum sample of the cancer patient prior to cancer therapy or treatment;
(b) determining if the uPA levels of the patient are increased compared to the serum uPA levels in normal controls; the normal control serum uPA level being a value of 1924 pg/ml; and
(c) establishing that the metastatic cancer patient having increased uPA levels compared with the uPA levels of normal controls has one or more of (i) ongoing or progressing metastasis; (ii) a likelihood of a decreased or poor response to cancer therapy or treatment; and (iii) a shorter survival outcome.

14. The method according to claim 13, wherein the metastatic cancer is a metastatic solid tumor cancer.

15. The method according to claim 13, wherein the metastatic cancer is selected from the group consisting of metastatic cancer of the skin, lung, trachea, breast (mammary), prostate, cervix, ovary, vulva, vagina, endometrium, bladder, pancreas, gall bladder, thyroid, esophagus, head and neck, brain, kidney, liver, stomach, rectum, or colon cancer.

16. The method according to claim 13, wherein the metastatic cancer is metastatic breast cancer or metastatic prostate cancer.

17. The method according to claim 13, wherein the uPA level is determined using an enzyme linked immunosorbent assay (ELISA).

18. The method according to claim 13, wherein the uPA levels in the patient's sample are determined in conjunction with the determination of the levels of one or more oncoprotein markers, and further wherein the levels of the one or more markers are correlated with patient outcome.

19. The method according to claim 18, wherein the one or more oncoprotein markers is selected from the group consisting of HER-2/neu, epidermal growth factor receptor (EGFR), complexed PSA (cPSA), p53 autoantibody, the breast cancer marker CA15-3 and the colon cancer marker CA19-9.

20. A method of determining if a cancer patient is a candidate for anti-plasminogen activation system cancer therapy, comprising:
(a) measuring the level of plasminogen activator inhibitor-1 (PAI-1) or the level of a complex of plasminogen activator and plasminogen activator inhibitor-1 (uPA:PAI-1 complex) in a plasma sample of the cancer patient;
(b) determining if either the level of PAI-1 or the level of uPA:PAI-1 complex in the plasma sample of the cancer patient is elevated compared to the normal level of PAI-1 or the normal level of uPA:PAI-1 complex in the plasma of normal controls; and
(c) if said determining step (b) indicates that either said level of PAI-1 or said level of uPA:PAI-1 complex in the plasma sample of the cancer patient is elevated above said normal level of PAI-1 or above said normal level of uPA:PAI-1 complex, selecting the patient having elevated plasma PAI-1 level and/or elevated plasma uPA-PAI-1 complex level as a candidate for anti-plasminogen activation system therapy;
wherein the normal plasma level of PAI-1 is a normal control value of about 63 ng/ml; and
wherein the normal plasma level of uPA:PAI-1 complex is a normal control value of 293 pg/ml.

21. The method according to claim 20, wherein the anti-plasminogen activator system therapy is selected from serine protease inhibitors or uPA receptor antagonists.

22. The method according to claim 21, wherein the serine protease inhibitor is an amidino phenylalanine-type serine protease inhibitor.

23. The method according to any one of claims 1, 5, 9, 13, or 20, wherein the anti-cancer treatment or therapy is administered in combination with at least one biologically active agent, and further wherein the biologically active agent is selected from one or more of i) drugs; ii) hormones; or iii) synthetic compounds.

24. The method according to claim 23, wherein the drug is epirubicin.

25. The method according to claim 20, wherein the patient and normal plasma PAI-1 levels are determined by an enzyme linked immunosorbent assay (ELISA).

26. The method according to claim 20, wherein the cancer patient has a solid tumor cancer.

27. The method according to claim 20, wherein the cancer patient has a cancer selected from breast cancer, colon cancer, lung cancer, ovarian cancer, or prostate cancer.

28. The method according to claim 20, wherein the patient and normal plasma uPA:PAI-1 complex levels are determined by an enzyme linked immunosorbent assay (ELISA).

29. The method according to claim 20, further comprising measuring the level of plasminogen activator (uPA) in a serum sample of the cancer patient, and wherein an elevated level of uPA in the serum sample of the cancer patient compared to uPA normal levels in normal serum controls indicates an enhanced likelihood of the cancer patient benefiting from therapies targeting components of the plasminogen activation system.

30. The method according to claim 29, wherein the normal serum uPA level is a normal control value of 1924 pg/ml.

31. A method of monitoring cancer progression, or the efficacy of cancer treatment or therapy, in a cancer patient, comprising:
(a) measuring the levels of one or more of the following plasminogen activator (PA) system analytes in a body fluid sample from the cancer patient: (i) uPA analyte in a serum sample, (ii) PAI-1 analyte in a plasma sample; and (iii) uPA:PAI-1 complex analyte in a plasma sample; and
(b) determining if the sample levels of one or more of the uPA, PAI-1, or uPA:PAI-1 complex analytes in the cancer patient is increased or elevated during the cancer treatment or therapy compared to normal levels of each of the respective plasminogen activator system analytes in normal controls; wherein an increase or elevation in the sample levels of one or more of the uPA, PAI-1, or uPA:PAI-1 complex analytes in the cancer patient compared to the respective normal levels of the analytes during the monitoring period indicates one or more of the following: (i) cancer progression, (ii) a more severe stage of the cancer, or (iii) lack of response by the patient to the cancer treatment or therapy; and further wherein the cancer patient's sample uPA level is considered elevated or increased if it is above a normal uPA value of 1924 pg/ml; the cancer patient's sample PAI-1 level is considered elevated or increased if it is above a normal PAI-1 value of 63 ng/ml; and the cancer patient's sample uPA:PAI-1 complex level is considered elevated or increased if it is above a normal uPA:PAI-1 complex value of 293 pg/ml.

32. The method according to claim 31, wherein the cancer patient has a solid tumor cancer.

33. The method according to claim 31, wherein the cancer patient has a cancer selected from lung, breast (mammary), prostate, cervix, ovary, vulva, vagina, endometrium, bladder, esophagus, head and neck, kidney, liver, stomach, or colon cancer.

34. The method according to claim 33, wherein the cancer is breast cancer, ovarian cancer, colon cancer, lung cancer, or prostate cancer.

* * * * *